US009854203B2

(12) United States Patent
Benetti et al.

(10) Patent No.: US 9,854,203 B2
(45) Date of Patent: Dec. 26, 2017

(54) CONVERTIBLE TELEPRESENCE ROBOT

(71) Applicant: Orbis Robotics, Inc., Vista, CA (US)

(72) Inventors: Robert J. Benetti, Encinitas, CA (US); Robert A. Benetti, Encinitas, CA (US); Bryan T. Benetti, Encinitas, CA (US)

(73) Assignee: Orbis Robotics, Inc., Vista, CA (US)

( * ) Notice: Subject to any disclaimer, the term of this patent is extended or adjusted under 35 U.S.C. 154(b) by 0 days.

(21) Appl. No.: 15/148,881

(22) Filed: May 6, 2016

(65) Prior Publication Data

US 2016/0330402 A1 Nov. 10, 2016

Related U.S. Application Data

(60) Provisional application No. 62/157,555, filed on May 6, 2015.

(51) Int. Cl.
*G05B 19/18* (2006.01)
*H04N 7/14* (2006.01)
(Continued)

(52) U.S. Cl.
CPC ............... *H04N 7/142* (2013.01); *A61G 5/04* (2013.01); *A61G 5/125* (2016.11); *A61G 5/128* (2016.11); *A61H 3/04* (2013.01); *B25J 9/1676* (2013.01); *A61B 5/01* (2013.01); *A61B 5/021* (2013.01); *A61B 5/024* (2013.01); *A61G 2203/14* (2013.01); *A61G 2203/16* (2013.01); *A61G 2203/20* (2013.01); *A61H 2201/0107* (2013.01); *A61H 2201/0161* (2013.01); *A61H 2201/0176* (2013.01); *A61H 2201/0207* (2013.01); *A61H 2201/0214* (2013.01); *A61H 2201/0228* (2013.01); *A61H 2201/1635* (2013.01); *A61H 2201/5007* (2013.01); *A61H 2201/5043* (2013.01); *A61H 2201/5046* (2013.01); *A61H 2201/5048* (2013.01); *A61H 2201/5064* (2013.01); *A61H 2201/5066* (2013.01); *A61H 2201/5069* (2013.01); *A61H 2201/5084* (2013.01); *A61H 2201/5092* (2013.01); *A61H 2201/5097* (2013.01); *A61H 2230/08* (2013.01); *A61H 2230/30* (2013.01); *G01S 15/931* (2013.01); *G01S 17/936* (2013.01); *G05B 2219/45108* (2013.01); *G05B 2219/45117* (2013.01); *G08C 2201/93* (2013.01)

(58) Field of Classification Search
CPC ........ H04N 7/142; A61G 5/125; A61G 5/128; A61G 5/04; A61H 3/04; B25J 9/1676
See application file for complete search history.

(56) References Cited

U.S. PATENT DOCUMENTS

| 8,306,664 B1 * | 11/2012 | Wiley | ...................... B25J 5/007 280/304 |
| 2007/0129849 A1 * | 6/2007 | Zini | ................. G05B 19/41895 700/258 |

\* cited by examiner

Primary Examiner — Ian Jen
(74) Attorney, Agent, or Firm — Hulsey, P.C.

(57) ABSTRACT

The material contained in this disclosure pertains to robotics related to convertible robots incorporating telecommunication elements. Embodiments of the system and apparatuses described can facilitate instant communication with family and friends, health status monitoring and support from caregivers; and promote optimal health, longevity, and independent living by providing high-tech economical solutions at each stage of the aging process. Embodiments of the system and apparatuses may be converted from an independent telecommunications robot, to a robotic walker, to a robotic wheelchair.

19 Claims, 20 Drawing Sheets

(51) Int. Cl.
B25J 9/16 (2006.01)
A61G 5/04 (2013.01)
A61H 3/04 (2006.01)
A61G 5/12 (2006.01)
*A61B 5/021* (2006.01)
*A61B 5/024* (2006.01)
*A61B 5/01* (2006.01)
*G01S 15/93* (2006.01)
*G01S 17/93* (2006.01)

Table 3: CTR™ Telepresence Robot with Intelligent Walking Assistant and Intelligent Wheelchair

| Standard Features | | |
|---|---|---|
| | All features available in the Basic CTR™ Telepresence Robot are available in the CTR™ Telepresence Robot with Intelligent Walking Assistant and Intelligent Wheelchair. | |
| | Wheelchair can be remotely operated by a designated child or caregiver. | |
| | Wheelchair functions can be controlled2 by verbal commands | |
| | Seat folds down automatically to the sitting position when commanded verbally by the elder. | Prevents back strain and injury if the elder had to bend over to lower the seat. |
| | Seat extends out to assist the elder to sit down when commanded verbally by the elder | This helps an elder to transition from a standing to sitting position by supporting the weight of the elder as the chair lowers to the sitting position. |
| | Footrests automatically swing out when the elder sits in the chair and the chair is in the normally sitting position | This prevents the senior from tripping on the footrest when getting into the chair. |
| | Chair raises the elder to a standing position when verbally commanded by the elder if the elder's feet are off of the footrests. | This helps an elder to transition from a sitting to standing position by supporting the weight of the elder as the chair raises to the standing position. |
| | Joystick can be configured for left hand or right hand operation | |
| Health Monitoring & Diagnostics | | |
| Optional Features | | |
| | Thermoelectric beverage cooler and warmer is integrated in the armrests | |
| Safety Features | | |
| | Any current manual or automatic operation stops if the elder commands stop or yells loudly. | |
| | FPGA Safety rated controller | |

FIG 18

CONVERTIBLE TELEPRESENCE ROBOT

CROSS-REFERENCE TO RELATED APPLICATIONS

This application claims priority to Provisional Patent Application No. 62/157,555, filed May 6, 2015, which is hereby incorporated by reference in its entirety.

FIELD OF THE INVENTION

The subject matter contained in this document is related to the field of robotics, and more specifically in some embodiments pertains to robotics related to robots capable of being converted between multiple configurations and incorporating telecommunication elements.

BACKGROUND OF THE INVENTION

The subject matter included herein can facilitate instant communication with family and friends, health status monitoring and support from caregivers; and promote optimal health, longevity, and independent living by providing high-tech economical solutions at each stage of the aging process.

BRIEF SUMMARY OF THE INVENTION

In embodiments, the disclosure contained herein is related to a modular robotic system with different modules that may allow for customization of a base unit to fulfill different want and/or needs of a user throughout different stages of infirmity. Such customizable packages may allow for the base device to be re-configured as a walker, or a wheelchair.

Initially the elder may have physical mobility and require no external aides to get out of bed or chairs and walk. However, due to the normal mental and physical aging process it becomes increasingly difficult to operate computers, phones or other electronic products and appliances. For this need the system may be configured in its base configuration (see FIG. 1), whereby the system may act as a personal robotic assistant and telecommunications system.

As the aging process continues steady and safe walking becomes increasingly difficult, and the risk of injury from falling or tripping becomes a significant risk to longevity and independent living. Routine exercise, including walking, becomes a vital necessity to maintain optimal vascular circulation, lymph drainage, mental alertness and cognitive function, digestion, and cardiovascular health. For this need the system may be converted into a walker configuration through the addition of some modular components. In this configuration the system may provide the same functions as it does in its base configuration, but may also provide support for the individual while in an upright position, and may provide additional functionality based thereon.

At advanced age or due to obesity, accident, or other health conditions, a wheelchair can become a necessity to maintain quality of life and continued independent living. A manual wheelchair becomes impossible for an elder to maneuver due to the physical strength and dexterity required to control and maneuver the wheel chair. Just getting into and out of the wheelchair eventually becomes an impossible task. For this need the system may be converted in to a wheelchair configuration through the additional of some modular components. In this configuration the system may provide for the functions as it does in the base configuration, but may also provide support for the individual while in a seated position, and may provide additional functionality based thereon.

The system can be readily converted to between a base configuration, a walker configuration, and a wheelchair configuration. It offers an optimal solution to facilitate an elder during all stages of the aging process to maintain social communications, optimal health and brain function, increased longevity, and significantly extending the length of quality life and independent living.

BRIEF DESCRIPTION OF THE DRAWINGS

The novel features believed characteristic of the disclosed subject matter will be set forth in claims that are filed. The disclosed subject matter itself, however, as well as a modes of use, further objectives, and advantages thereof, will best be understood by reference to the following detailed description of an illustrative embodiment when read in conjunction with the accompanying drawings, wherein:

Figure 16:
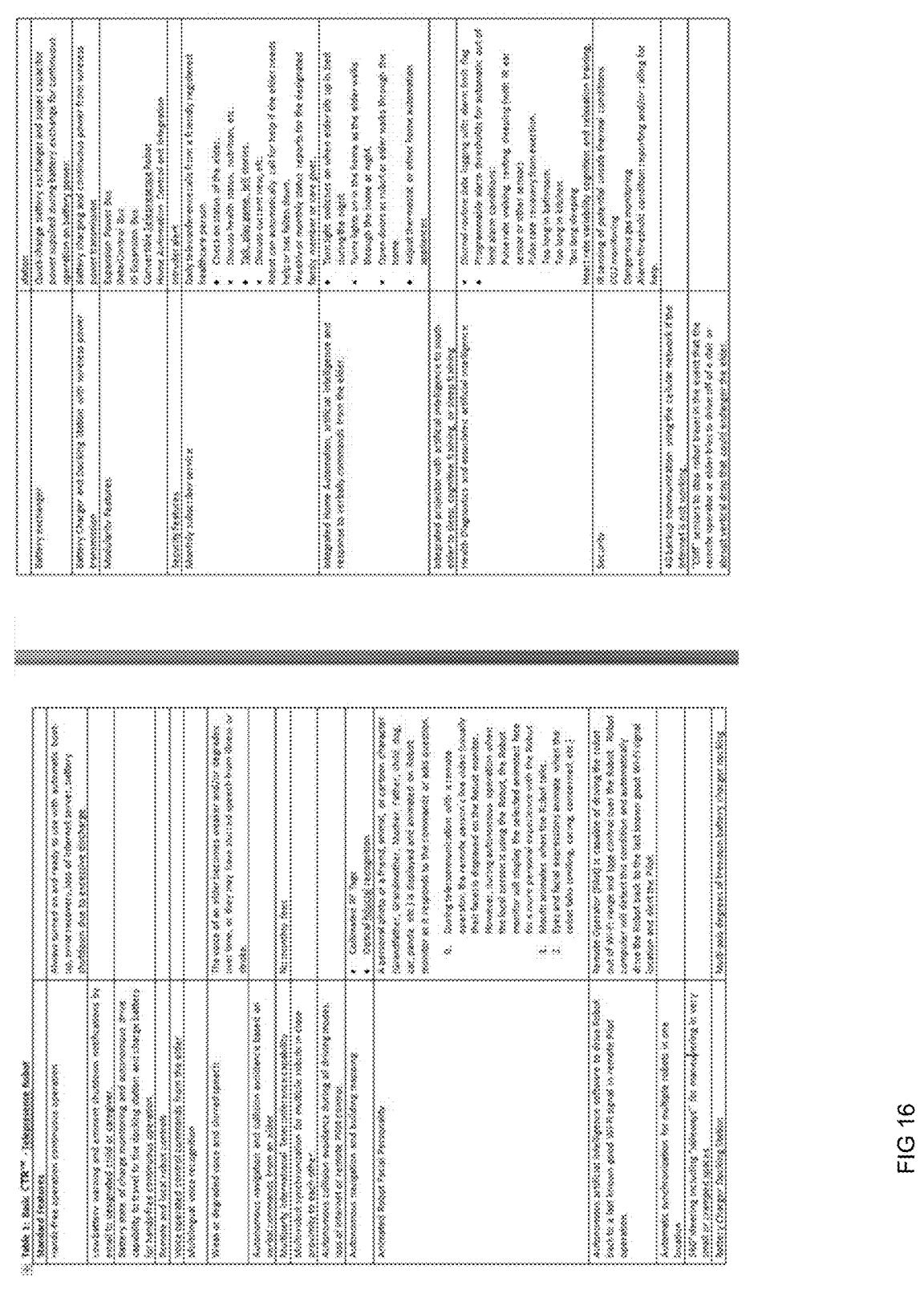

FIG. 16 depicts a chart showing examples of features that may be available when the system is in a base configuration.

Figure 17:
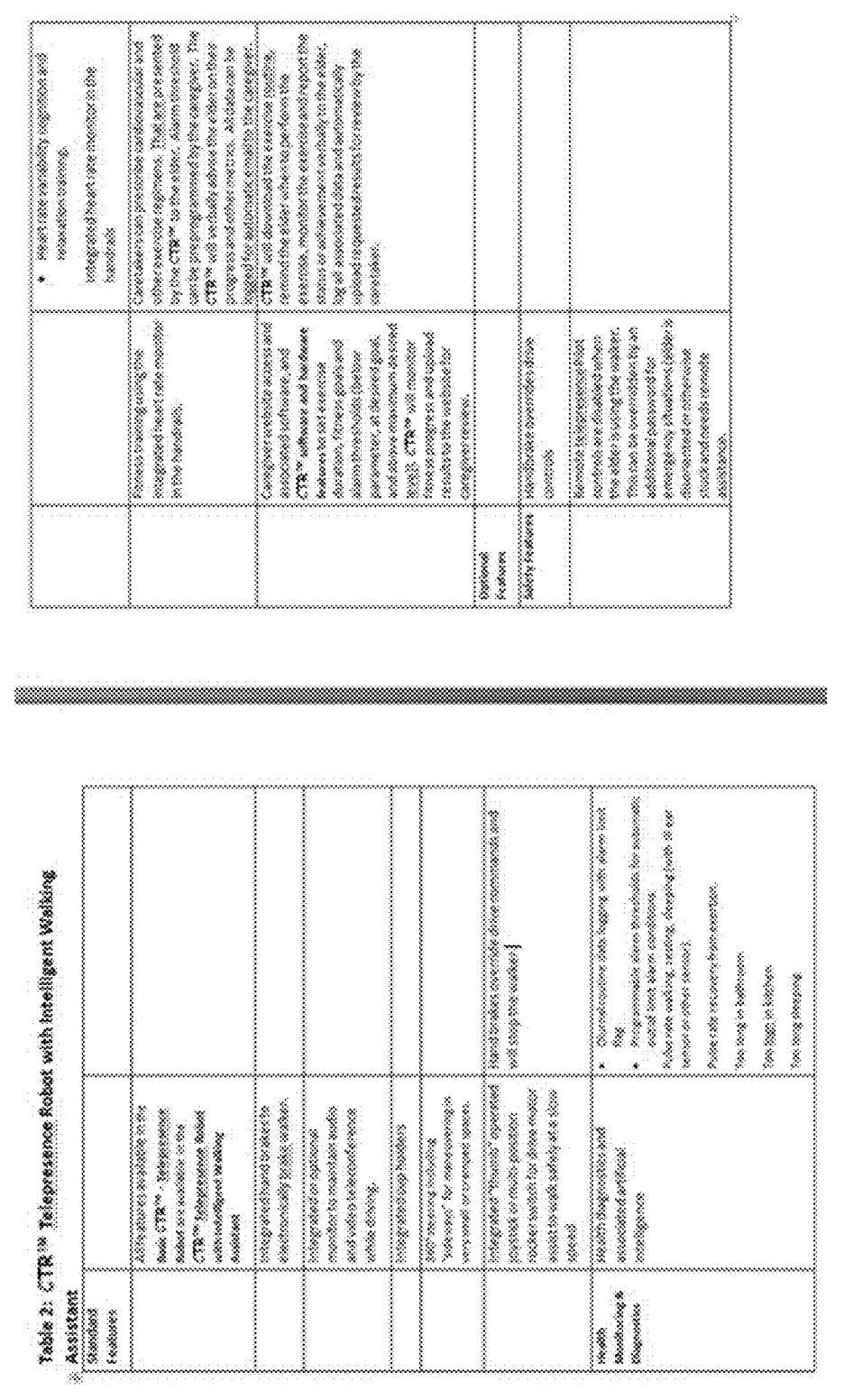

FIG. 17 depicts a chart showing examples of features that may be available when the system is in a walker configuration.

FIG. 18 depicts a chart showing examples of features that may be available when the system is in a wheelchair configuration.

DETAILED DESCRIPTION OF ILLUSTRATIVE EMBODIMENTS

Reference now should be made to the associated FIGUREs, in which the same reference numbers are used throughout the different FIGUREs to designate the same components.

It will be understood that, although the terms first, second, third, etc. may be used herein to describe various elements, these elements should not be limited by these terms. These terms are only used to distinguish one element from another element. Thus, a first element discussed below could be termed a second element without departing from the teachings of the present disclosure.

Figure 1:
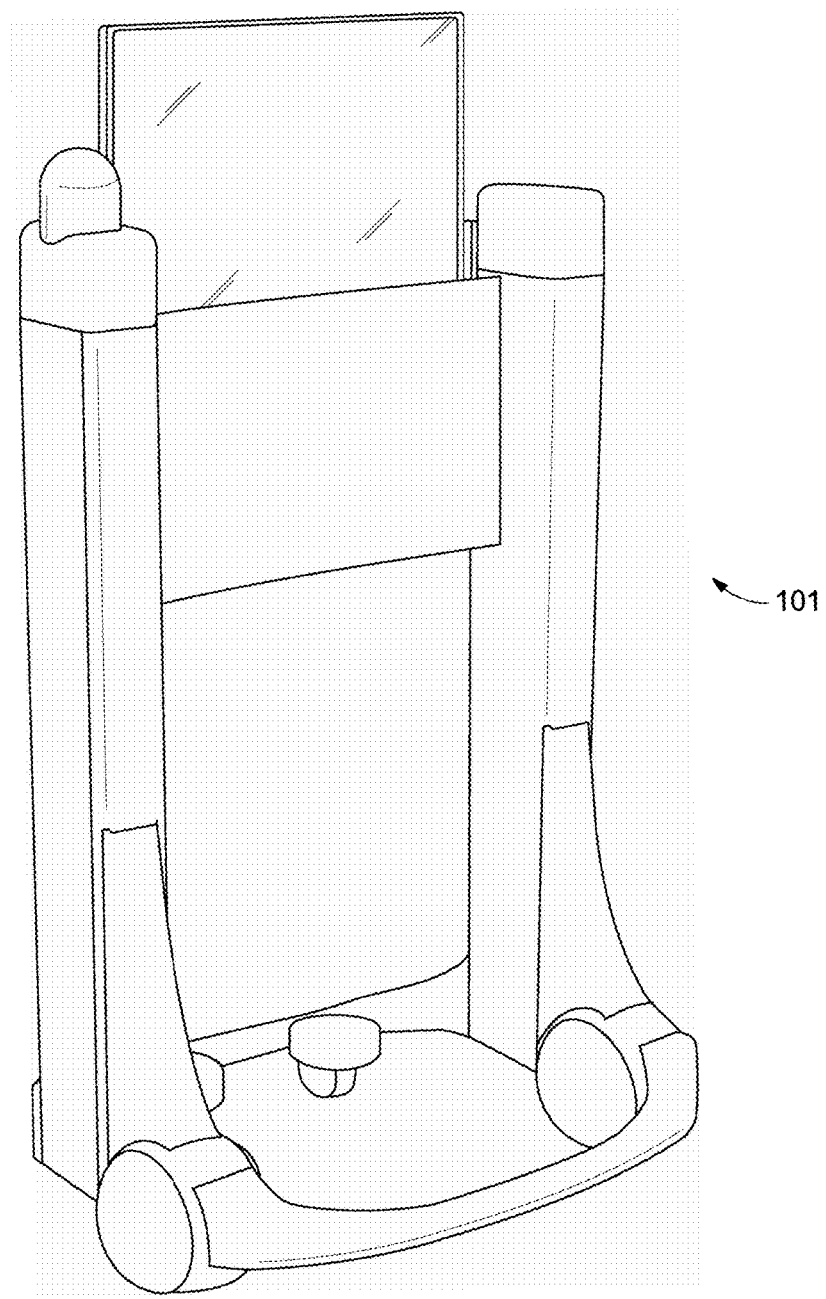
FIG. 1 depicts an exemplary embodiment of the system in a base configuration.

FIG. 1 depicts an embodiment of the base configuration 100 of a convertible telepresence robot system 101. In this base configuration 100 the system 101 may move through the ambient environment through the use of motorized primary wheels and an array of sensors and processors which may be used to detect and avoid potential obstacles. These same sensors may allow the system to locate and automatically engage with a system for charging the system's onboard batteries.

Referring to FIG. 1, in an embodiment a system 101 may include a hands free operation element. The hands free operation element may provide for continuous operation. Such a hands free operation element may be configured to maintain the system in an always-on status and ready for immediate use without delay for: powering on, system boot-up, loss of wireless communications link or connection to a server, or system shutdown due to inadequate battery state of charge or power level. Such a system may include a power management element including battery power level warning communications and shutdown warnings sent via communications such as email or text messaging to designated persons such as, for example, caregivers and responsible family members. In embodiments, such a system may include a battery state of charge or battery power level monitoring element which may provide for autonomous driving of the system to a docking station for recharging the battery at the docking station, and thus to permit continuous operation. In an embodiment as shown, a system may include remote robotic control elements, local robotic control elements, autonomous robotic control elements, or semi-autonomous robotic control elements. In embodiments, such a system may include voice command elements for control by a user, such as an elderly or infirm person. A voice control element may enable control with degraded or slurred speech. In embodiments, a system may include a navigation element that may enable autonomous navigation or semi-autonomous navigation of the system, collision avoidance, or navigation upon voice command by the user. A navigation element may include a pilot feature and map-building feature. In embodiments, a system may include a synchronization element for synchronizing operations and availability with other similar or identical robotic system units, for example, to provide for availability of systems in a large facility with multiple users.

In an embodiment, a system may include animated robot facial personality functionality. In embodiments, for example, a system may include a displayed photographic or other visual representation of family members, caregivers, friends, pets or other animals, or cartoon characters, and which may be animated on a monitor 1, 26 of the system during voice and listening communications with the user, or signaling communications such as waving or pointing with the user. In embodiments, live video of a remote operator or remote assistant may be provided. In embodiments, a mouth may be animated when the system speaks to a user. In embodiment, eyes and facial expressions may be animated when the robot speaks to indicate concern, care or other expressions.

Figure 2:
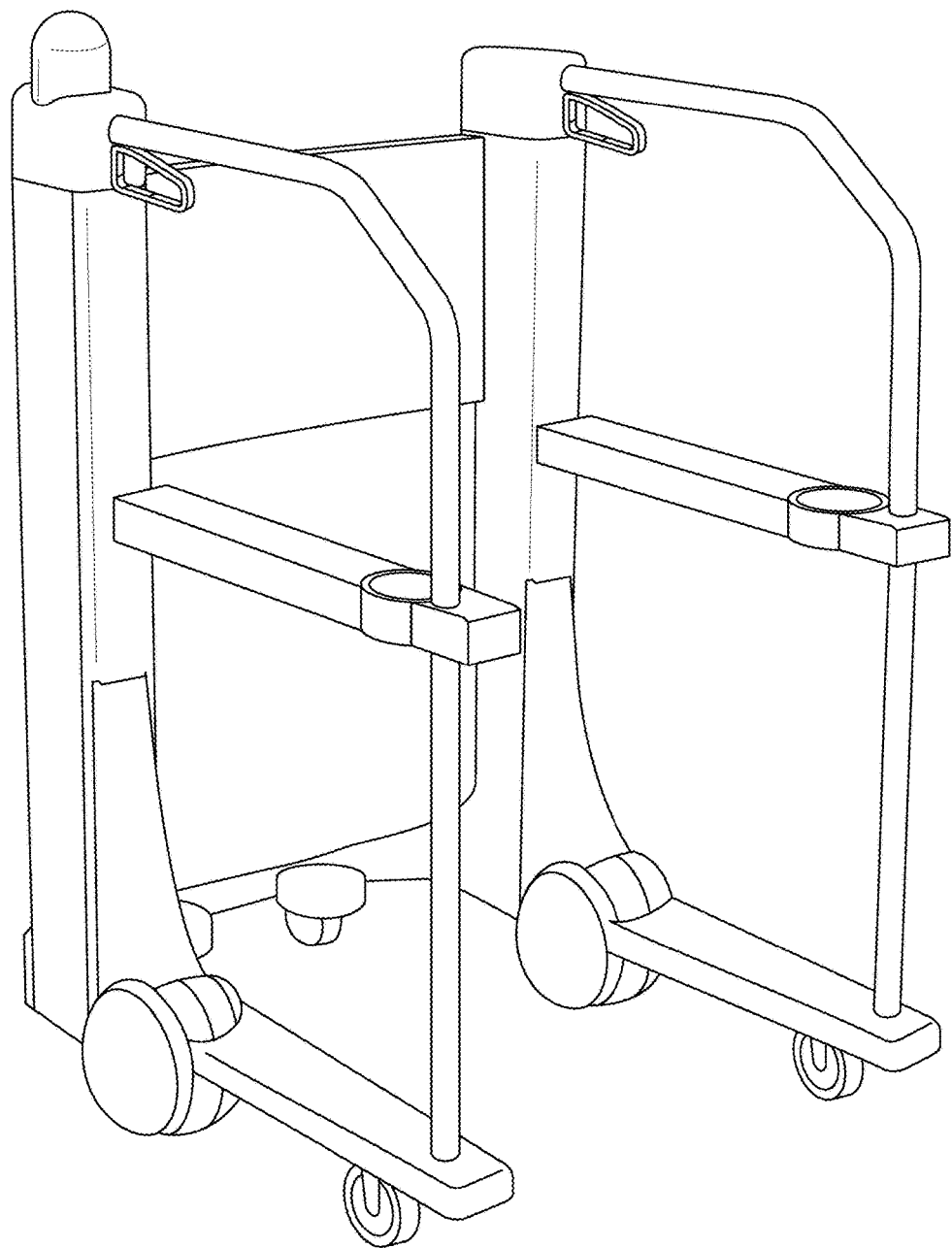
FIG. 2 depicts an exemplary embodiment of the system in a walker configuration.
Figure 7:
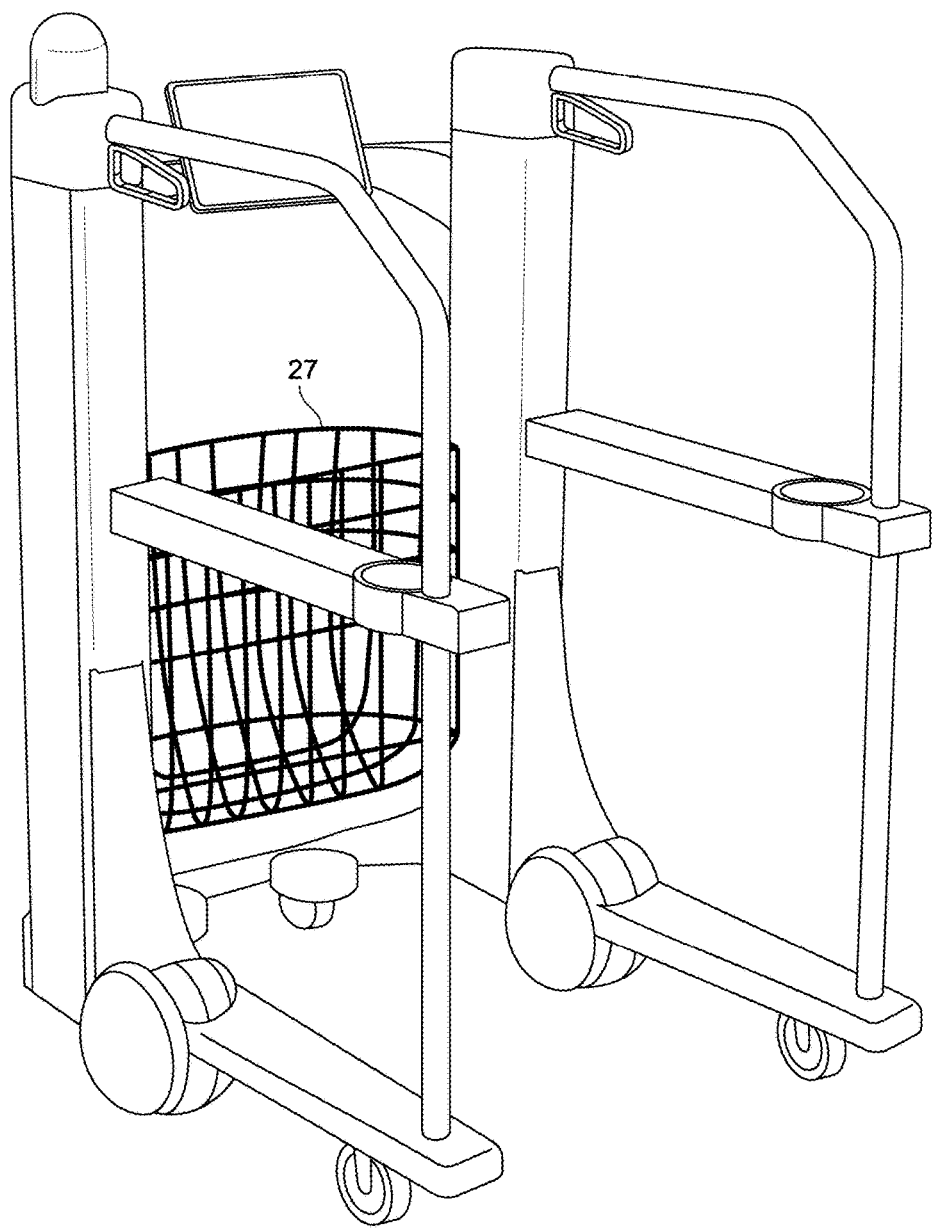
FIG. 7 depicts an exemplary embodiment of the system in a walker configuration, having an optional small monitor and utility basket.

FIG. 2 depicts an embodiment of the system configured for use as a walker 200. Railing extensions 13 may be coupled to the drive columns 4, 7 of the base configuration 100 in order to provide the framework for supporting a user while in an upright position. Embodiments of the walker configuration 200 of the system may comprise blood pressure and pulse monitoring sensors in the railing extension 13 so that the system may monitor the user's vital signs while the system is in use. The walker configuration 200 may additionally comprise one or more hand actuated brakes 18, which may be positioned below, or otherwise near, the top end of the railing extensions 13 in order to be proximate to the location of the user's hands. Embodiments of the walker configuration 200 of the system may provide for one or more cup-holders 28 integrated into one or both of the upper lateral supports 16. Such cup-holders 28 may be configured to electrically heat or cool beverages retained, optionally, include a storage basket (as can be seen in FIG. 7), which may be supported in-between the drive columns 4, 7, and extend in a direction opposite the lateral supports 16, 17.

Figure 3:
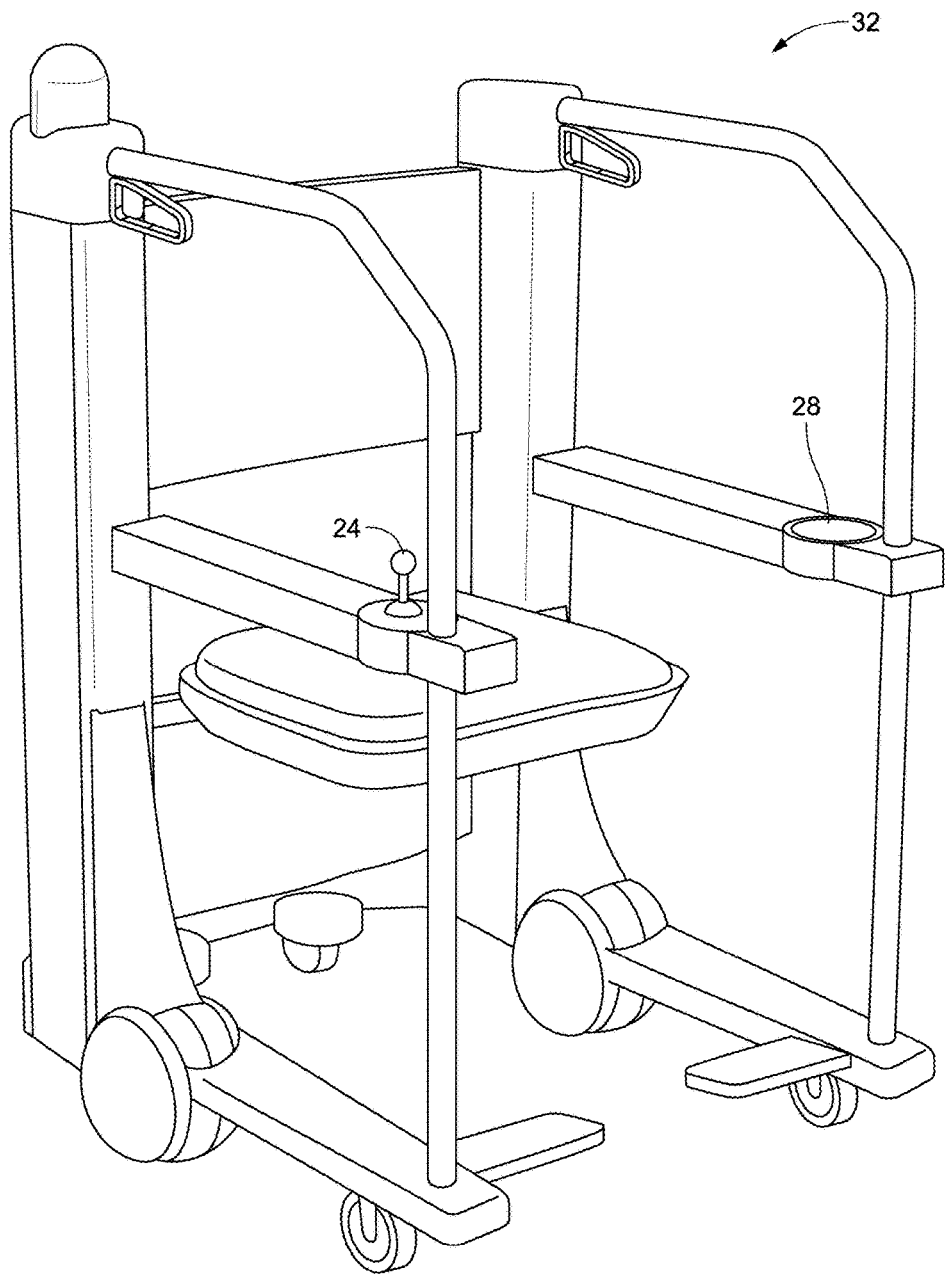
FIG. 3 depicts an exemplary embodiment of the system in a wheelchair configuration.
Figure 4:
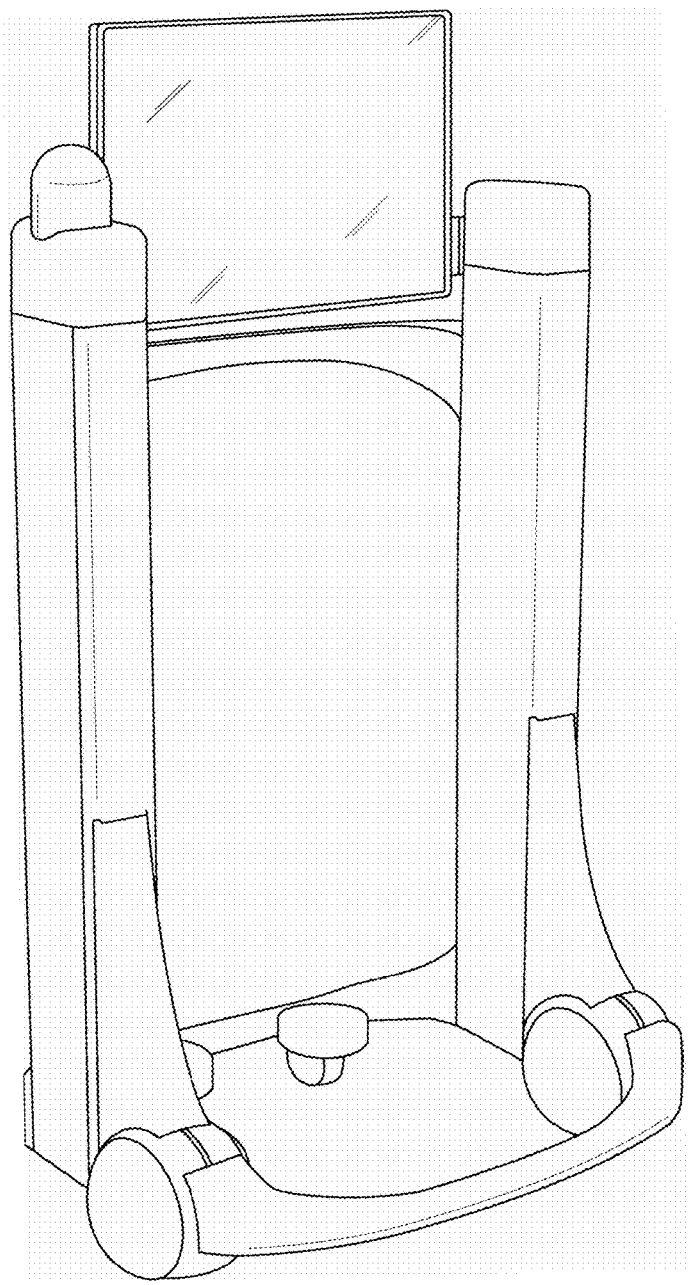
FIG. 4 depicts an exemplary embodiment of the system in a base configuration with the monitor portion of the system in a raised position.
Figure 5:
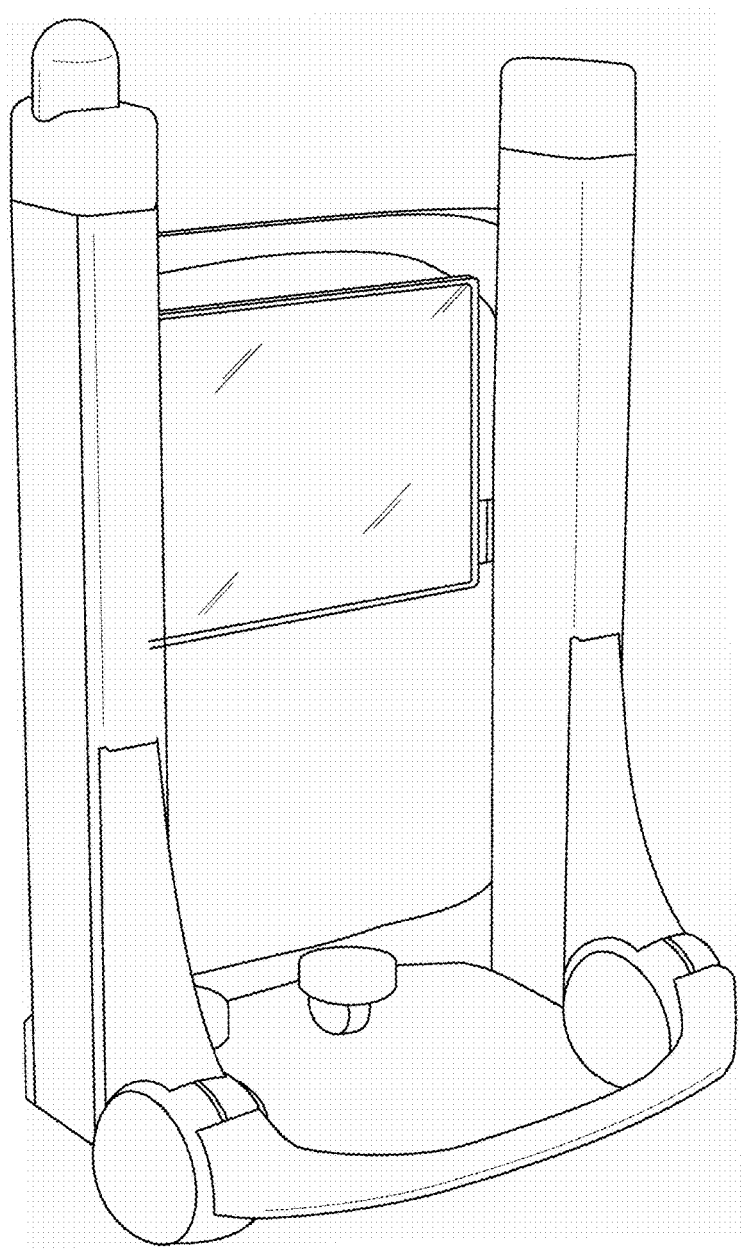
FIG. 5 depicts an exemplary embodiment of the system in a base configuration with the monitor portion of the system in a lowered position.
Figure 8:
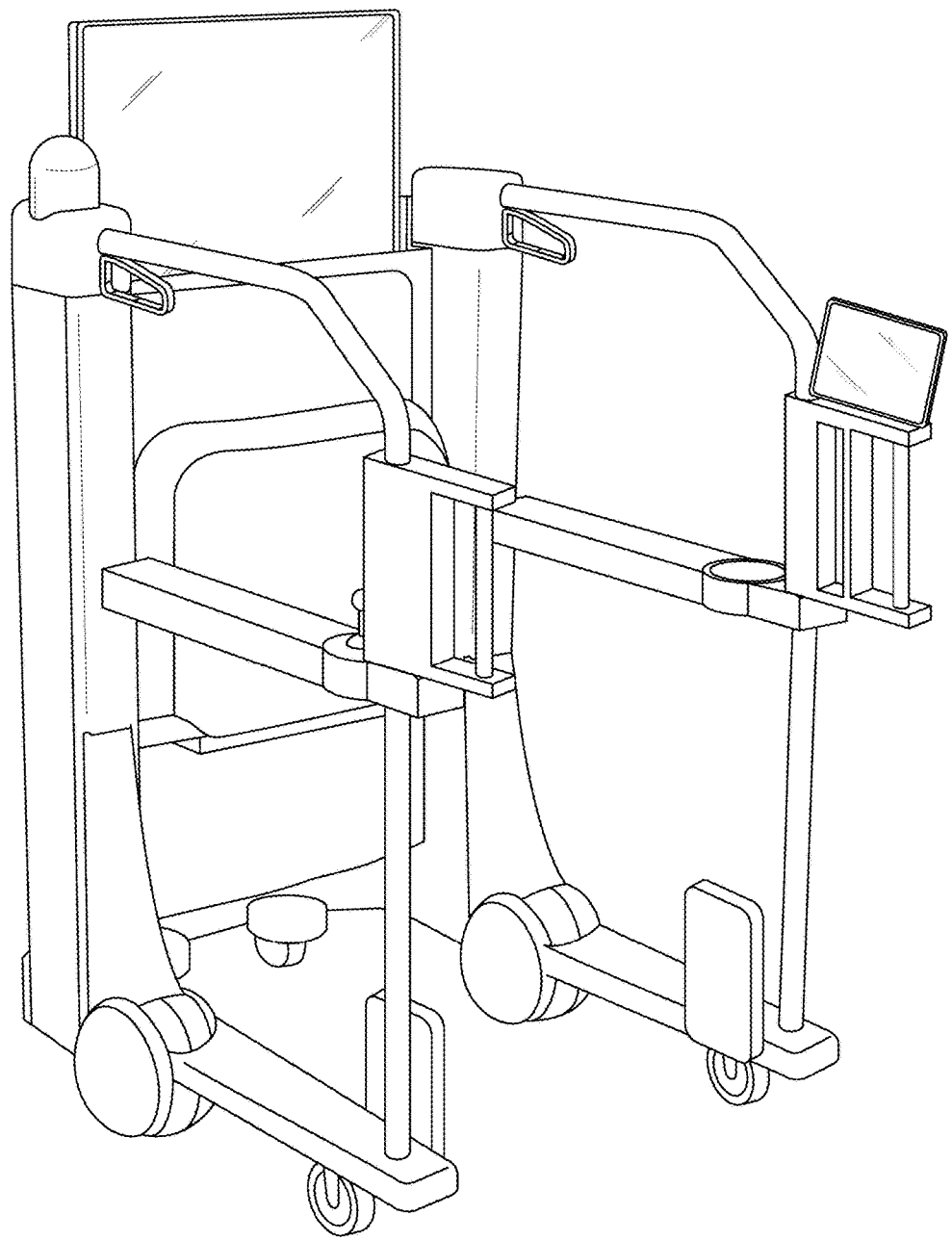
FIG. 8 depicts an exemplary embodiment of the system in a hybrid walker/wheelchair configuration wherein the system has the wheelchair portions added, but retains the handbrakes available in the walker configuration. In this figure the seat and foot supports of the wheelchair portion are in their retracted/stowed positions and the main monitor of the system is deployed.

FIG. 3 depicts an embodiment of the system configured for use as a wheelchair 300. A seat portion 22 and foot supports 23 may be coupled to the base configuration 100 (this may also require the addition of railing extensions 13) or to the walker configuration of the system in order to allow for support of the user while in a seated position. In embodiments, the seat portion 22 and foot supports 23 may be configured such that they may be rotated about a hinge to move from a vertical, stowed, position (as can be seen in FIG. 8) to a horizontal, deployed, position (for accepting and supporting the rear-end and feet of the user when in a seated position; see FIG. 3). Embodiments may be configured to have the seat portion 22 and/or the foot supports 23 to transition from a deployed to a stowed position in response to an action by the user. Cup-holders 28 may be provided in a manner identical to that of the walker configuration 200 described above. Embodiments may additionally comprise a user control 24 for receiving user input and in response control the movement of the system. In embodiments, the user system 24 may comprise a joystick integrated with one of the upper lateral supports 16. In embodiments the wheelchair configuration of the system may additionally comprise a secondary monitor 26 (see FIGS. 6 and 8), which may be pivotally and rotatable attached to one of the railing extensions 13 such that the user of the wheelchair configuration 300 of the system may view the secondary monitor while seated on the system. Embodiments of the wheelchair configuration 300 of the system may additionally comprise one or more hand grips 25 affixed to the railing extensions 13.

The hand grips 25 may be positioned at a point on the railing extensions 13 that is above the upper lateral supports 16.

Figure 6:
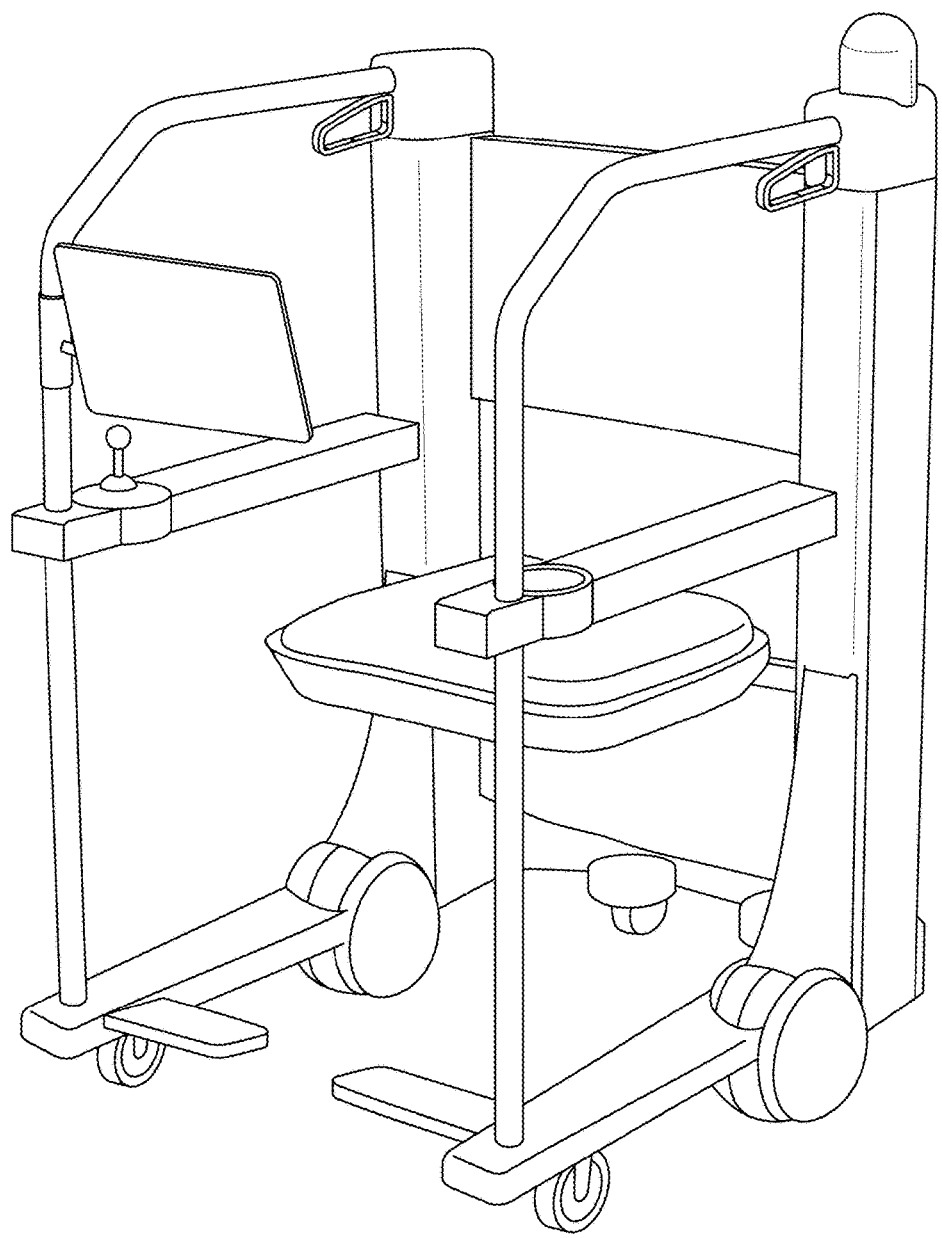
FIG. 6 depicts an exemplary embodiment of the system in use while in the wheelchair configuration.

FIG. 6 depicts an individual seated in the system while it is in its wheelchair configuration 300.

Figure 10:
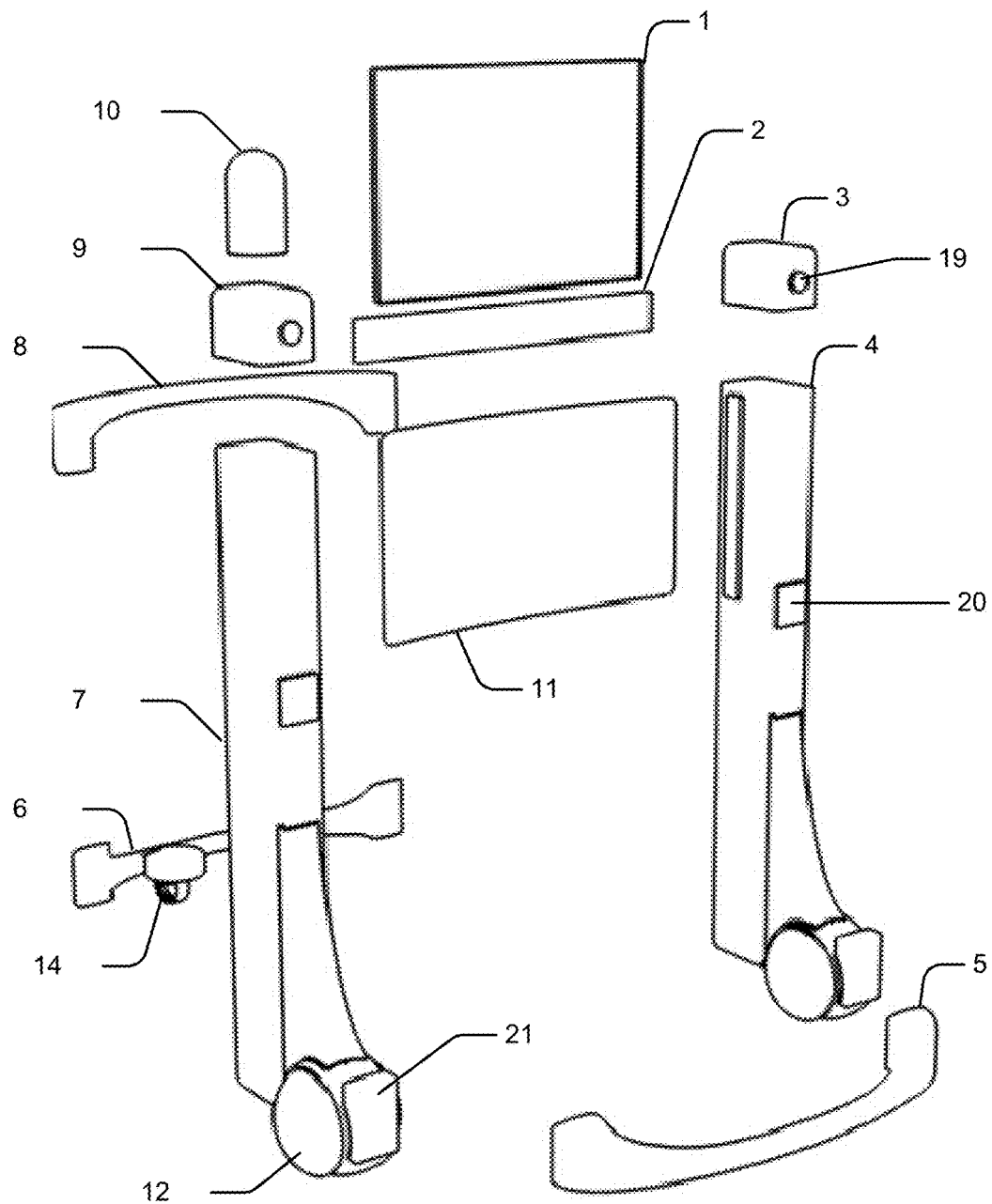
FIG. 10 depicts a diagrammatic exploded view of an exemplary embodiment of the system in a base configuration.
Figure 11:
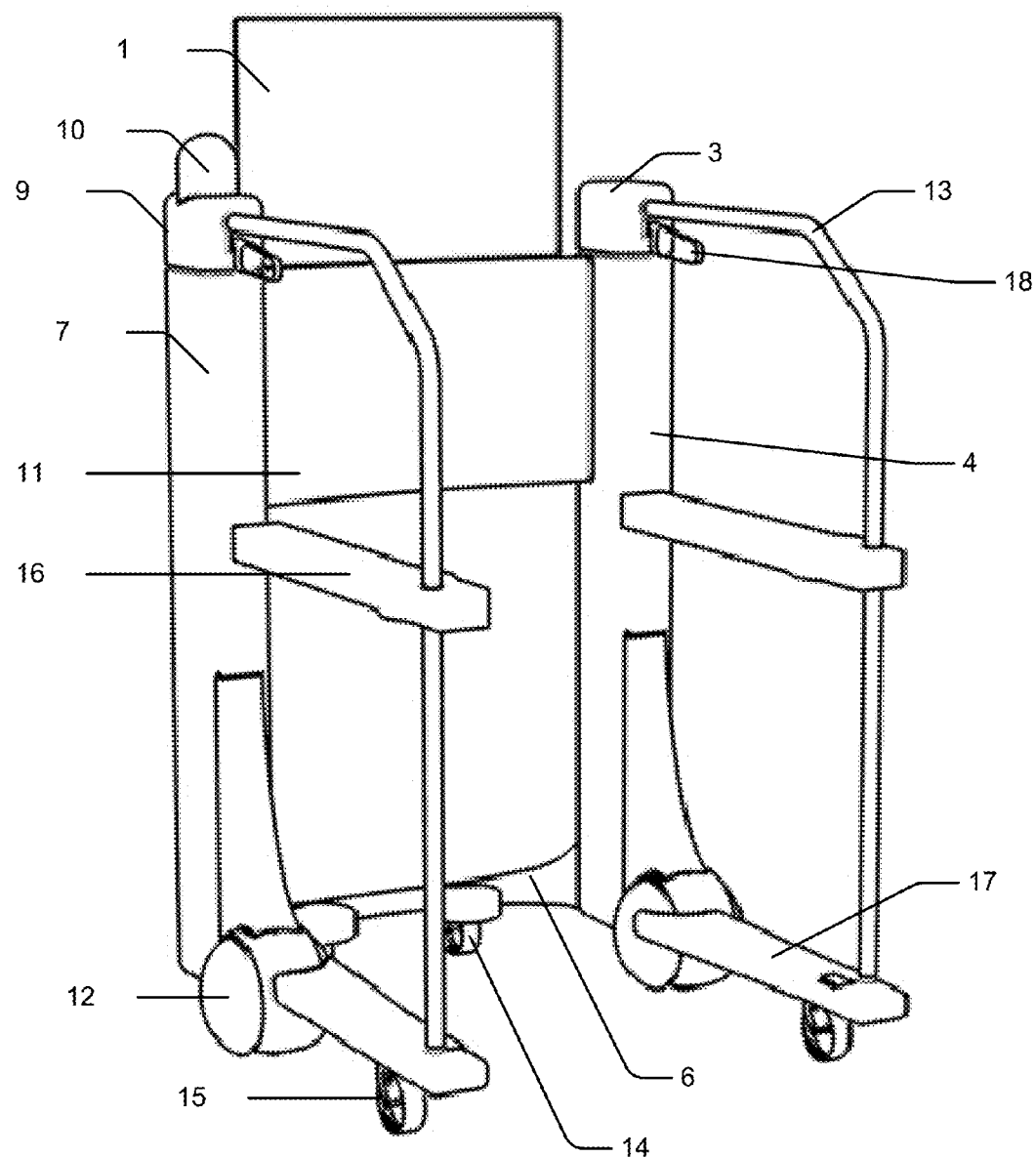
FIG. 11 depicts a diagrammatic perspective view of an exemplary embodiment of the system in a walker configuration.

FIG. 10 depicts an exploded view of an embodiment of the base configuration 100 of the system, wherein different component elements are shown separated from one another. Note that not all elements are numbered or shown separate. In the embodiment of the base configuration 100 of the system depicted in FIG. 10 monitor 1 may be attached to a top side of monitor bracket 2. The connection of monitor 1 to monitor bracket 2 may be at least one of a hinged, pivotable, rotatable, and disconnectable attachment. A bottom side of monitor bracket 2 may be attached to support panel 11. The right and left sides of support panel 11 may be attached to the right drive column 4 and left drive column 7 respectively. Drive columns 5 and 7 may comprise a drive motor assembly, a battery module, a battery charger, a battery charger connection, a controller board, a wiring harness, a speaker assembly and a microphone array (see FIGS. 19, 20). The bottom end of drive columns 5 and 7 may be disconnectably attached to a front safety bumper 5 and a lower-rear safety bumper 6. Lower-rear safety bumper 6 may comprise a secondary wheel 14 assembly. The secondary 14 and tertiary wheels 15 may be unpowered caster wheels. An upper-rear safety bumper 8 may be attached to an upper portion of drive columns 5 and 7. The right and left drive columns 5 and 7 may have column top portions 3 and 9 attached to them at their top end. A camera 10 may be attached to one or more of the column top portions 3 and 9. The camera 10 may be a pan/tilt/zoom camera. The attachments between the constituent elements of the system may be disconnectable in order to facilitate addition and/or removal of the system's modular components.

Figure 14:
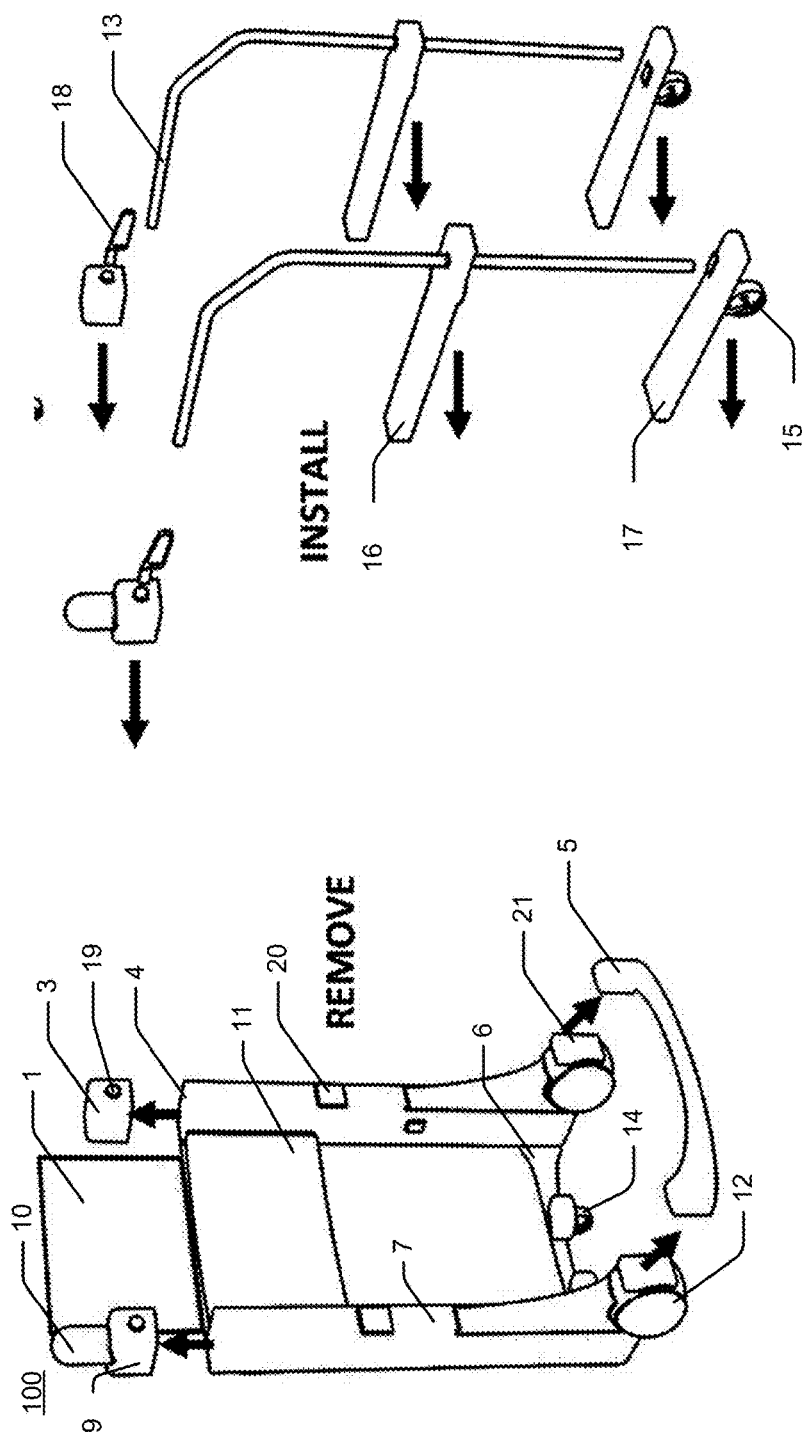
FIG. 14 depicts an exemplary process by which modular components may be removed from and/or added to the base configuration of the system to convert it to the walker configuration of the system.
Figure 15:
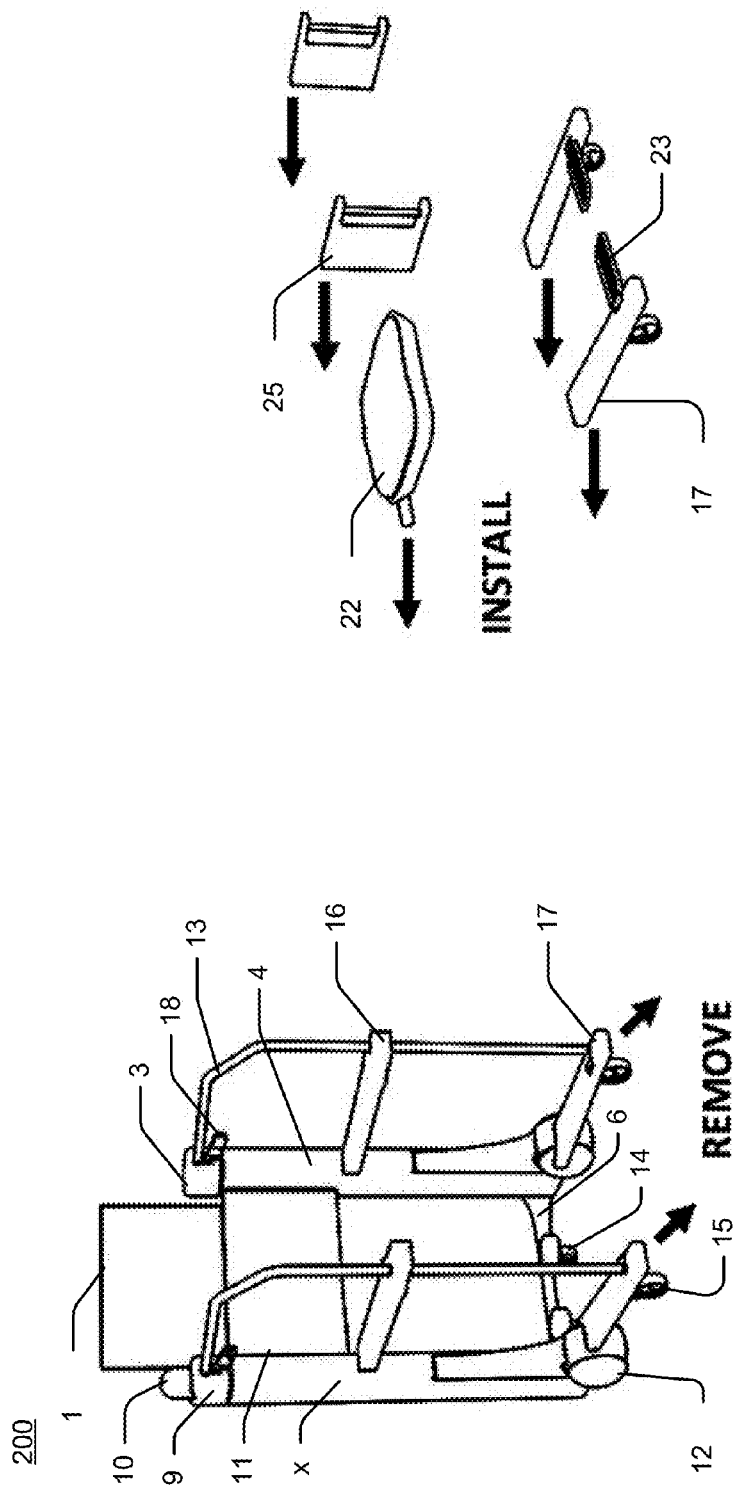
FIG. 15 depicts an exemplary process by which modular components may be removed from and/or added to the walker configuration of the system to convert it to the wheelchair configuration of the system.

Conversion of the system from the base configuration 100 (seen in FIG. 1) to the walker configuration 200 (seen in FIG. 2) or the wheelchair configuration 300 (seen in FIG. 3), or the walker/wheelchair hybrid configuration (seen in FIG. 8) may require the addition of modular components that may be provided separately from the base unit, allowing for upgrade and customization after purchase in order to conform to the user's changing needs/wants. Refer to FIGS. 14 and 15 to see conversion between the different system configurations.

Embodiments of the system may allow for remote access and control of the system through one or more communications network, such as but not limited to the internet. There may be multiple users who are authorized to access and control the system. This remote access may be enabled in all configurations of the system, but may be restricted in certain configurations if desired (it may not be ideal to give remote control to a remote user when an infirm individual is relying on the system for stability while use in its walker configuration 200).

The system may be used as a telecommunications platform through which users may contact remote individuals, or through which remote individuals may contact the user of the system.

The system may comprise at least one powered wheel (primary wheel 12). Additionally, the system may comprise at least one unpowered wheel (secondary 14 or tertiary wheels 15). The at least one powered main wheel 12 may be configured to enable the system to travel under its own power, and may be configured to enable the system to travel straight forwards and backwards, as well as directly side to side (laterally).

The system may be configured to actively, or upon specific instruction, monitor one or more aspects of the user.

Embodiments of the system may comprise a microphone and may be programmed to respond to a database of pre-established or user-customizable voice commands. The voice commands ability may be limited to only the voice of the user of the system and/or other authorized users. Examples of such verbal commands may include, but are not limited to, "come here", "seat down", "charge", "turn off", "call", etc.

In embodiments of the wheelchair configuration 300 of the system the seat portion may be configured to fold up and down automatically based on data from the system's sensors. The seat portion 22 may extend outward and retract to assist the user with the actions of sitting on and getting up from being seated on the seat portion 22 of the wheelchair configuration 300 of the system.

Conversion of the base system 100 to any other configuration of the system may not impede or disrupt the communication functionality of the system. This may be due to the fact that the components necessary for at least a portion of the sensing and processing abilities of the system are included in the base configuration 100 of the system. Accordingly, the addition of the modular packages to convert the system to a different configuration may not detract from the functionality of the system.

Embodiments of the walker 200 and wheelchair configurations 300 of the system may comprise armrests (upper lateral supports 16). The armrests may comprise cup-holders, which may in turn comprise a thermoelectric beverage cooler/warmer.

Figure 19:
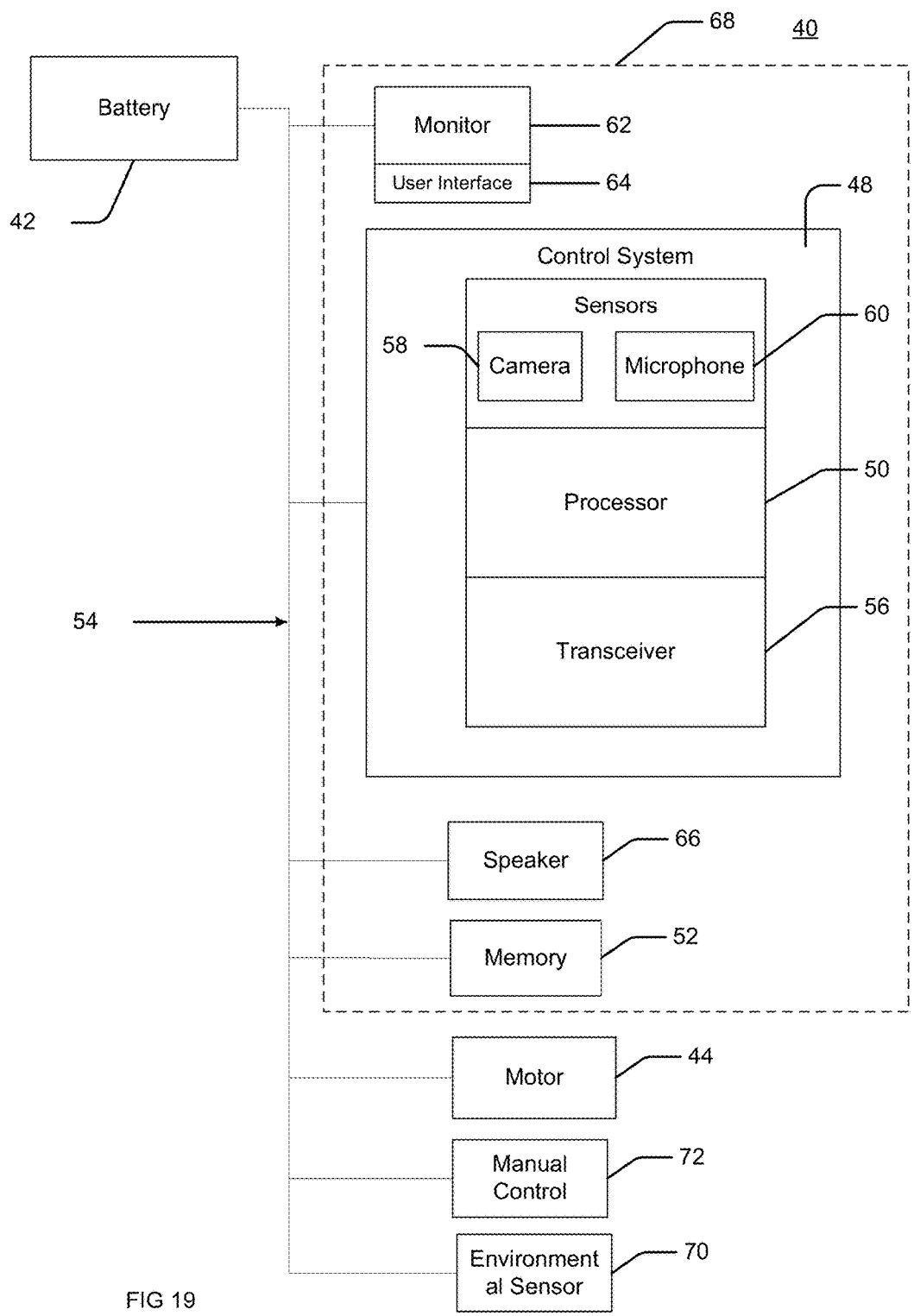
FIG. 19 illustrates a simplified exemplary electrical system in accordance with embodiments of the system.
Figure 20:
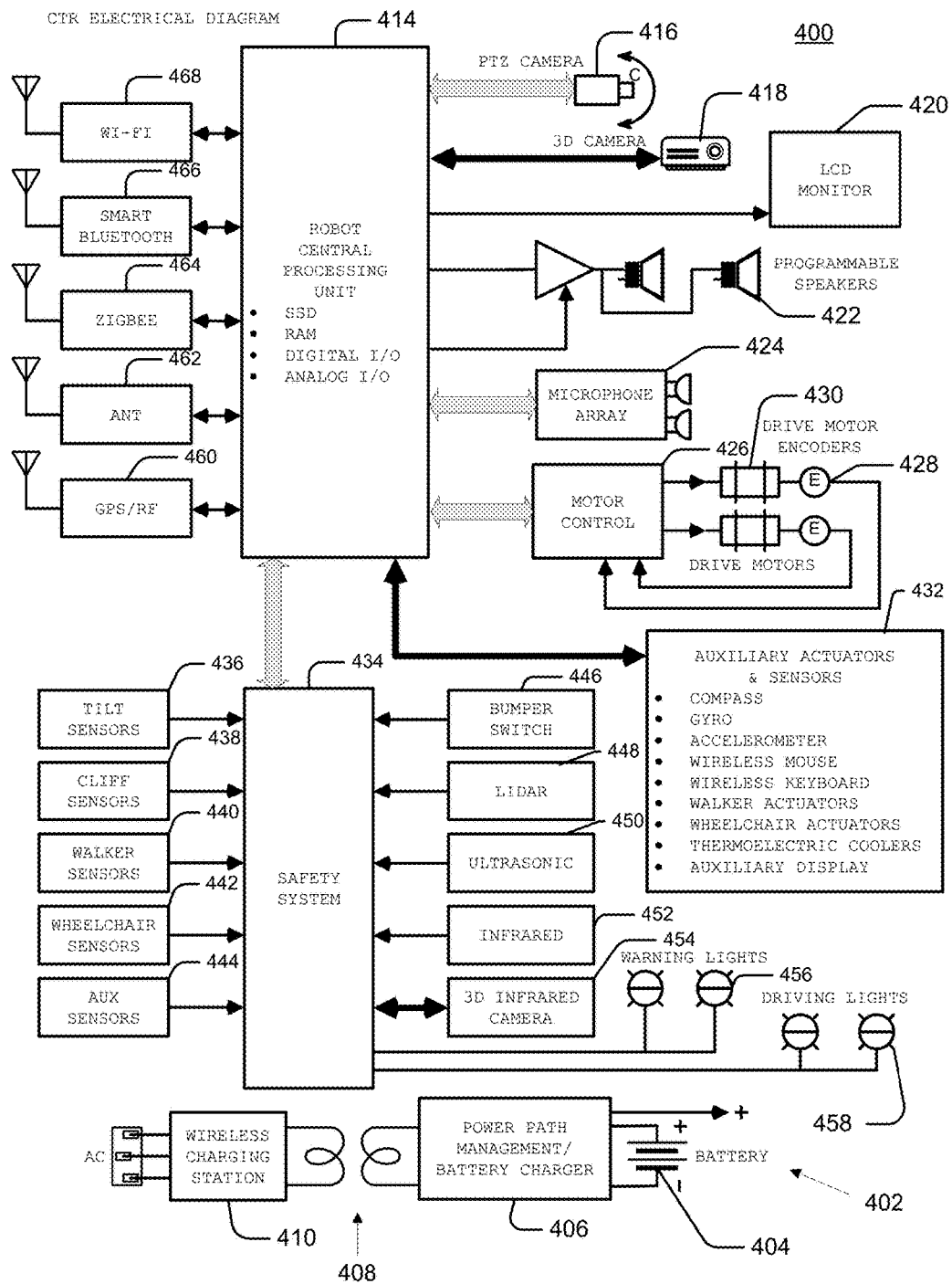
FIG. 20 illustrates a more detailed exemplary electrical system in accordance with embodiments of the system.

In reference to FIGS. 19 and 20, embodiments of the electrical systems 40 and 400 contained in the convertible robotic system may comprise a plurality of sensors, such as but not limited to, a camera 58, infra-red sensors 452, blood pressure monitoring sensors, pulse monitoring sensors, etc. The plurality of sensors may be connected to a processor 50, 414, which may be used to control the activity of the sensors and to interpret the signals generated by the sensors.

In reference to FIG. 8, in embodiments the system may still be used as a walker after having been converted to the wheelchair configuration 300. To achieve this walker/wheelchair hybrid configuration, the system may allow for the seat portion 22 and foot supports 28 present in embodiments of the wheelchair configuration 300 to be stowed when not in active use. This stowage of the seat portion 22 and foot supports 28 may provide for an unobstructed space in which the user could stand and which would allow the user to use the system in same manner as the walker configuration 200 despite its having been converted to the wheelchair configuration 300.

Referring to FIG. 19, in an embodiment, convertible telepresence robot system 100 may include electrical system 40. Electrical system 40 may include a rechargeable battery power supply 42 for supplying power to an electric motor 44 via a suitable power supply circuit (not shown in FIG. 19). Electric motor 44 may be controlled by a control system 48. Control system 48 may include a processor 50 operably coupled to memory 52, such as via a system bus 54. In an embodiment, not shown, control system 48 may include one or more microprocessors or PLC's (not shown). Control system 48 may include a control software application (not shown) including executable code stored in memory and executable by processor 50 to control operation of electric motor 44 for stopping and starting the same. In some embodiments, processor 50 may control speed of electric motor 44 or an assembly including such an electric motor.

Figure 12:
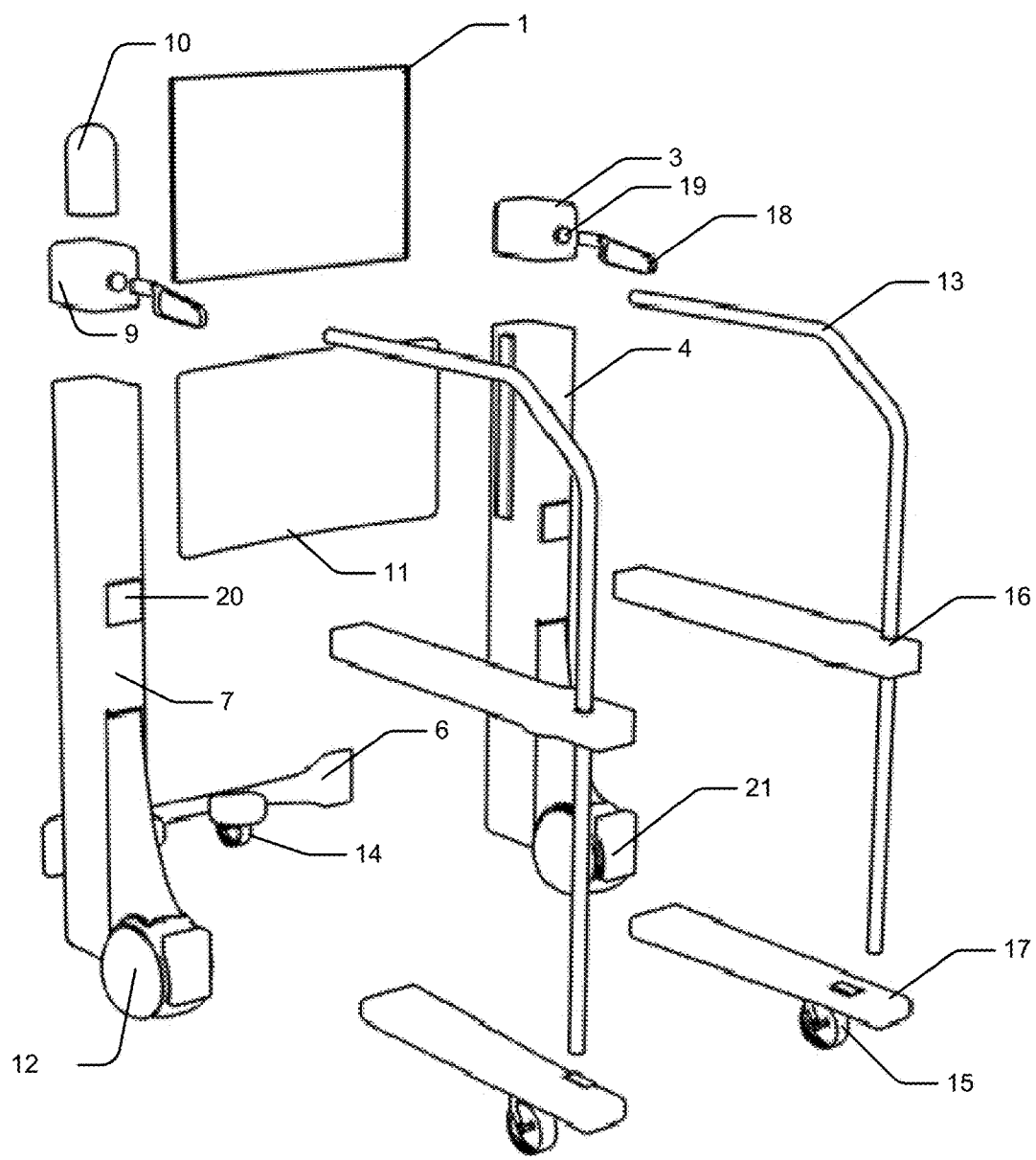
FIG. 12 depicts a diagrammatic exploded view of an exemplary embodiment of the system in a walker configuration.
Figure 13:
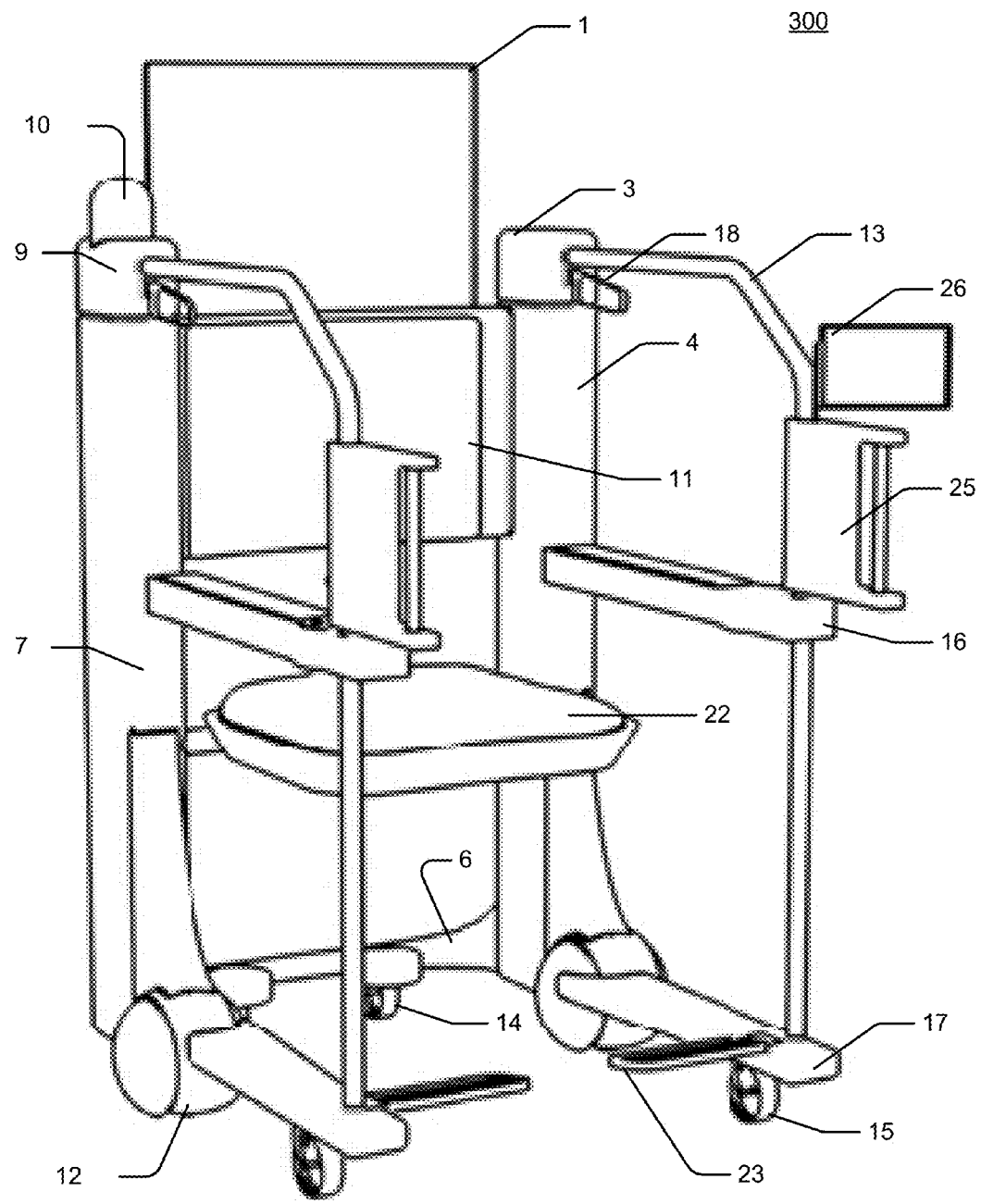
FIG. 13 depicts a diagrammatic perspective view of an exemplary embodiment of the system in a wheelchair configuration.

Control system 48 may include a control software application and processor 50 operable for controlling propelled rolling movement of a primary wheel 12 driven by electric motor 44, for starting, stopping and controlling speed and direction of the convertible telepresence robot system 100 for rolling across a floor (not shown). It will be understood that a convertible frame assembly 32 (shown in FIGS. 12, 13) thus can be propelled by primary wheel 12 in controlled movement across the floor.

Referring to FIG. 19, control system 48 may include a transceiver 56 configured for wireless communication according to a suitable wireless communication protocol. It will be understood that transceiver 56 may be configured for communication via one or more wireless communication protocols such as, for example, Wi-fi, cellular, and Bluetooth. The transceiver 56 may be operable with or may include a network adapter and one or more communications protocol stacks. Transceiver 56 may be operable for communication with a local or remote computing device or server, or other compatible device such as, for example, a smartphone, tablet, smart watch, or pendant.

Control system 48 may include sensors such as a camera 58 and microphone 60. Sensors such as camera 58 may collect information for controlling operations of convertible telepresence robot system 101, such as propelled movement across a floor. Control system 48 may include a display monitor 62, which may be a flat screen display. Control system 48 may include a user interface 64 for displaying information and/or receiving user input. It will be understood that user interface 64 may include a touch screen input device, which may be provided in combination with a flat screen display as discussed herein above. In embodiments, control system 48 may include a wireless device such as a smartphone or wireless tablet computing device 68 having a touchscreen display interface, camera, microphone, speaker, processor, memory, transceiver and battery. Control system 48 may include an environment sensor 70 for collecting information for controlling operations of convertible telepresence robot system 101, such as for collision avoidance control during propelled movement across a floor. Environment sensor 70 may include, for example, a LIDAR sensor, ultrasonic sensor, infrared sensor, bumper switch, 3D infrared sensor, tilt sensor, cliff sensor, walker sensor, wheelchair sensor, auxiliary sensor, or any sensor accessible via a suitable communication interface (see FIG. 20). Environment sensor 70 may provide information to processor 50, such as via system bus 54. Control system 48 may include, for example, a collision avoidance subsystem (not shown in FIG. 19) including environment sensor 70 for collecting and providing environment information to a collision avoidance module (not shown in FIG. 19). Such a collision avoidance module may include a collision avoidance software application stored in memory 52 and executable by processor 50. Control system 48 may include manual control system 72. In some embodiments, manual control system 72 may override operation of other control components of control system 48 upon receiving manual user input, such as from a joystick controller or buttons (not shown in FIG. 19).

Figure 9:
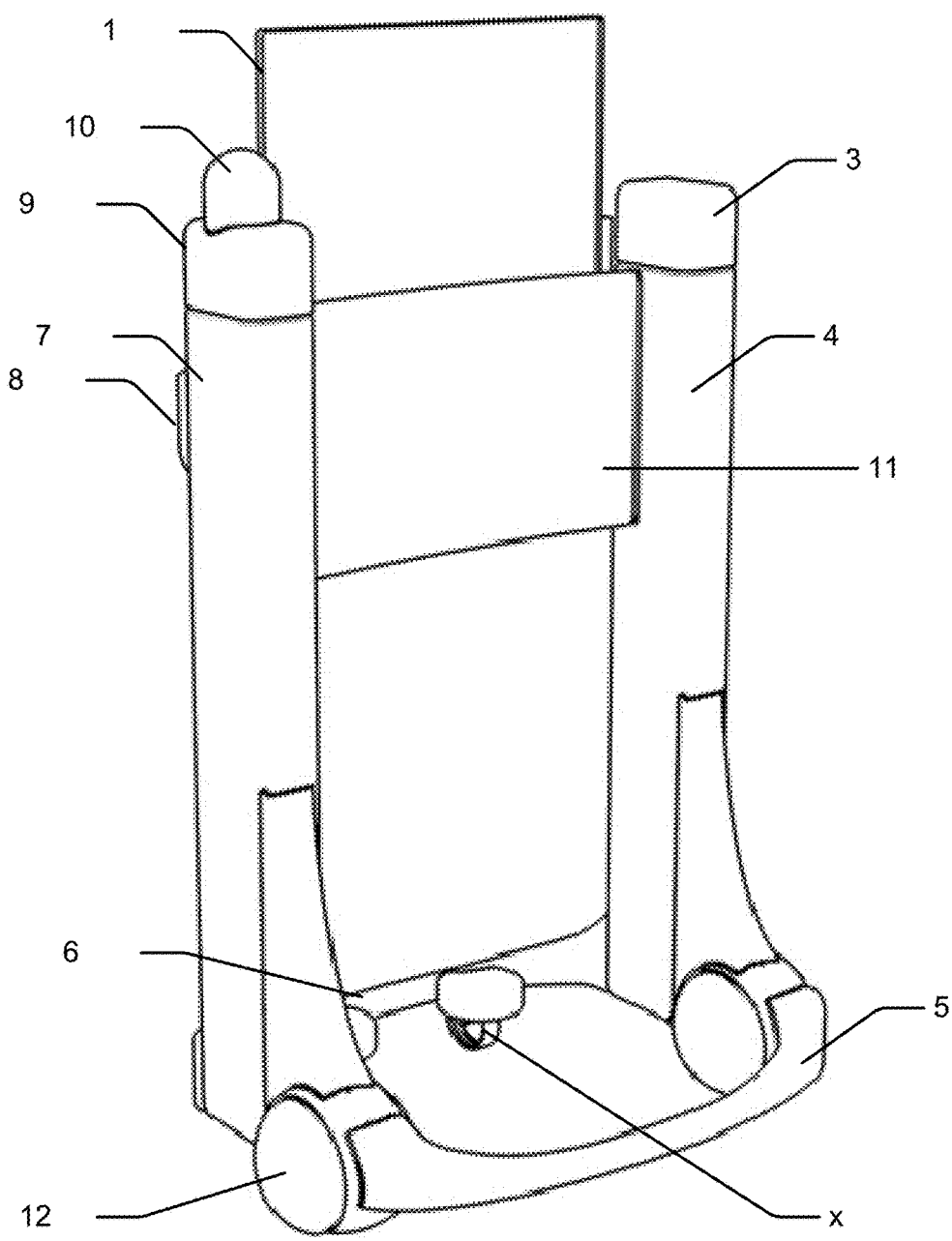
FIG. 9 depicts a diagrammatic perspective view of an exemplary embodiment of the system in a base configuration.

In reference to FIG. 9, embodiments of the base configuration 100 of the convertible telepresence robot system, which may operate autonomously from the user may comprise a monitor 1, a monitor bracket 2, a right column top portion 3, a right drive column 4, a front safety bumper 5, a lower-rear safety bumper 6, a left drive column 7, an upper-rear safety bumper 8, a left column top portion 9, a support panel 11, a left and a right primary wheel 12, at least one secondary wheel 14, and a plurality of sensors, which may include one or more of, but is not limited to a camera 10, a microphone, a pulse sensor, a blood pressure sensor, and one or more object proximity sensors.

In the base configuration 100 of the system the support panel 11 may be supported at a first end by the left drive column 7, and a second end, opposite the first end, by the right drive column 4. The lower-rear safety bumper 6 may be connected to a lower rear portion of a bottom end portion of the left drive column 7 and to a lower rear portion of a bottom end portion of the right drive column 4. The upper-rear safety bumper 8 may be connected to an upper rear portion of a top end portion of the left drive column 7 and to an upper rear portion of a top end portion of the right drive column 4. A first primary wheel 12 may be rotatably connected to a front portion of the bottom end portion of the left drive column 7 and a second primary wheel 12 rotatably connected to a front portion of the bottom end portion of the right drive column 4. The front safety bumper 5 may be rotatably engaging at least one secondary wheel 14. In embodiments there may be more than one secondary wheel 14 attached to the front safety bumper 5. In embodiments the secondary wheel(s) 14 may be unpowered caster wheels. The front safety bumper 5 may comprise two ends, each of the two ends respectively disengageably connected to one of the primary powered wheels 12 at a lower receiver point 21. A monitor bracket 2 may engage a top portion of the support panel 11. Visual aspects of the telecommunications capability of the system may be facilitated by the inclusion of a monitor 1 supported by the monitor bracket 2. In embodiments the monitor 1 may be connected to the monitor bracket 2 by a hinge that may allow for rotation of the monitor 1 in one or more axes. In embodiments the monitor bracket 2 may connected to the support panel 11 by a hinge that may allow for the rotation of the monitor bracket 2, and thereby the monitor 1, in one or more axes. Embodiments of the system may provide for a camera 10 that may be engageable with a top surface of at least one of the left column top portion 9 and the right column top portion 3.

The system may, when converted from the basic configuration 100 to the walker configuration 200 (see FIG. 14), additionally include left and right railing extensions 13, left and right upper lateral supports 16, left and right lower lateral supports 17, left and right tertiary wheels 15, and at least one hand brake 18. Additionally, when converting between the basic configuration 100 and the walker configuration 200, the front safety bumper 5 may be removed in order to allow for an open, unobstructed, space for the user's legs and feet.

In the walker configuration 200 a first end of the left lower lateral support 17 may be removably coupled to the left primary wheel 12. A bottom surface of the left lower lateral support 17 may be rotatably connected to the left tertiary wheel 15, a first end of the right lower lateral support 17 may be removably coupled to the right primary wheel 12, and a bottom surface of the right lower lateral support 17 may be rotatably connected to the right tertiary wheel 15. A first end of the left upper lateral support 16 may be removably coupled to the left drive column 7 at an upper receiver point 20, and a first end of the right upper lateral support 16 may also be removably coupled to the right drive column 4 at an upper receiver point 20. A top end of the left railing extension 13 may be removably connected to the left column top portion 9, and bottom end of the left railing extension 13 may be removably connected to a top surface of the left lower lateral support 17. The left railing extension 13 may traverse an aperture in the left upper lateral support 16 at a point between the top end of the left railing extension 13 and the bottom end of the left railing extension 13. Similarly, a top end of the right railing extension 13 may be removably connected to the right column top portion 3, and a bottom end of the left railing extension 13 may be removably connected to a top surface of the right lower lateral support 17. The right railing extension 13 may traverse an aperture in the right upper lateral support 16 at a point between the top end of the right railing extension 13 and the bottom end of the right railing extension 13. In order to allow for braking of the system while it is in its walker configuration 200 the at least one hand brake 18 may be removably engaged with at least one of the left column top portion 9 and the right column top portion 3 at a point below the top end of the respective railing extension 13. In embodiments the at least one hand brake 18 may be electronically connected to one or more of the primary 12, secondary 14, or tertiary 15 wheels. In addition, or in the alternative, embodiments may provide for the at least one hand break 18 to be mechanically connected to one or more of the primary 12, secondary 14, or tertiary 15 wheels.

When the system is converted from the walker configuration 200 to the wheelchair configuration 300, the system may further include a seat portion 22, a left foot support 23, a right foot support 23, and a user control. In such a wheelchair configuration 300 the seat portion 22 may be connected to and supported between the left drive column 7 and the right drive column 4 at a point between the upper-rear safety bumper 8 and the lower-rear safety bumper 6. The left foot support 23 may be connected to the left lower lateral support 17, and may extend towards the right lower lateral support 17. Similarly, the right foot support 23 may be connected to the right lower lateral support 17, and may extend towards the left lower lateral support 17. Additionally, in order to allow the user to control the movement of the wheelchair configuration 300 of the system while seated on the seat portion 22 the user control 24 may be integrated into at least one of the left upper lateral support 16 and the right upper lateral support 16.

For additional security, the wheelchair configuration 300 of the system may further comprise hand grips 25 affixed to the railing extensions 13 at a point above the upper lateral supports 16.

Since, when seated on the seat portion 22 of the wheelchair configuration 300 of the system, the user is facing away from the main monitor 1, the wheelchair configuration 300 of the system may include a secondary monitor 26 which may be pivotably connected to one of the railing extensions 13 such that it may be viewable by a user seated on the seat portion 22. In embodiments the secondary monitor 26 may be positioned on the railing extension 13 at a point above the hand grip 25.

In embodiments of the system the monitor bracket 2 may be configured to move up and down relative to the drive columns 4, 7, thereby allowing the monitor 1 to be raised or lowered.

As can be seen in FIG. 7, embodiments the system may comprise a storage basket 27 which may be connected to and supported the drive columns 4, 7 at a position between the lower-rear safety bumper 6 and the upper-rear safety bumper 8. If equipped the storage basket 27 should extend away from the space that the user would occupy when using the system in its walker or wheelchair configuration 300.

In embodiments of the wheelchair configuration 300 of the system the seat portion 22 may pivot from a first position in which the seat portion 22 is coplanar with a plane defined by the left drive column 7 and the right drive column 4 (vertical/stowed position) to a second position in which the seat portion 22 is perpendicular to the plane defined by the left drive column 7 and the right drive column 4 (horizontal/deployed position). Similarly, in embodiments of the wheelchair configuration 300 of the system the foot supports may pivot from a first position in which the foot supports 23 are coplanar with a plane defined by the lower lateral supports 17 (horizontal/deployed position) to a second position in which the foot supports 23 are perpendicular to the plane defined by the lower lateral supports 17 (vertical/stowed position). When the seat portion 22 and the foot supports 23 are in their stowed positions the system may be in a wheelchair/walker hybrid configuration (see FIG. 8) in which the user may use the system as a walker despite having the components of the wheelchair configuration 300 of the system.

The walker 200 and the wheelchair configurations 300 of the system may include one or more cup-holders 28 integrated into at least one of the upper lateral supports 16. In embodiments such cup-holders 28 may use electricity to heat and/or cool objects retained therein.

Embodiments of the system may provide for one or more of a heart rate sensor, a blood pressure sensor, and a thermal sensor, integrated into at least one of the left railing extensions 13.

Embodiments of the may be configured such that the wheels, and in particular the primary wheels 12, which are powered by the motor, may rotate in a horizontal axis to enable the system to move laterally (sideways).

When in the wheelchair configuration 300 the system may provide for the user control 24 that comprises a joystick.

Embodiments of the system may include a convertible telepresence robot system comprising a configurable frame assembly 32, and a set of wheels supporting the configurable frame assembly 32 for rolling movement across a floor. The set of wheels may comprise at least one primary wheel 12 powered for driving engagement with the floor. The system may include a battery power supply 42 supported for movement in common with the configurable frame assembly 32 relative to the floor. There may be an electric motor 44 operably connected to the battery power supply 42, the electric motor 44 may be in driving relationship with the one or more primary wheels 12 so that it may power rolling movement of the convertible telepresence robot system relative to the floor. The system may have a control system 48 comprising a processor 50 coupled to memory 52 and operable for executing a drive system control algorithm to control movement of the primary wheel 12 to selectably start and stop rolling movement of the convertible telepresence robot system relative to the floor, the control system 48 comprising a collision avoidance (environmental) sensor 70 and a collision avoidance algorithm to stop driving motion of the one or more primary wheels 12. The configurable frame assembly 32 may be selectively configurable between an independent assistive base configuration 100, a walker configuration 200 including railing extensions 13, and a wheelchair configuration 300 including a seat portion 22.

In embodiments, when in the walker configuration 100, the control system 48 may be configured to receive walking position information from one or more sensors.

While in the walker configuration 200, embodiments of the system may provide for the monitor 1 to be supported by the convertible frame assembly 32, facing a point between and above the railing extensions 13.

In embodiments, the system may have the battery power supply 42 and the electric motor 44 housed within a drive column member 4, 7 of the convertible frame assembly 32.

The system may be configured to have the drive column member 4, 7 support a respective upper end portion of the railing extensions 13.

The system may, in embodiments, have the drive column member 4, 7 supported by the primary wheel 12 at a bottom end portion of the drive column member 3, 7.

FIG. 20 illustrates aspects of an electrical system 400 of a convertible telepresence robot in an embodiment. Electrical system 400 may be identical to electrical system 40 shown in FIG. 19 and described hereinabove, except as may be otherwise described hereinbelow or shown in FIG. 20. Electrical system 400 may include a power supply system 402 having a rechargeable battery 404 and power path management module 406 managing a battery charger system 408. Battery charger system 408 may be functionally compatible with, or may include, a wireless charging station 410.

Electrical system 400 may include control system 412. Control system 412 may include robot central processing unit 414. Robot central processing unit 414 may include a processor, memory, system bus and communications transceiver as described for electrical system 49 (shown in FIG. 19). Referring again to FIG. 20, control system 412 may include PTZ camera 416 and 3D camera 419 for collecting visual image information. Control system 412 may include monitor, such as an LCD monitor 420 for displaying information for the user. Control system 412 may include programmable speakers 422 for outputting audible information. Control system 412 may include a microphone array 424 for collecting audio information. Control system 412 may include a motor control system 426 for controlling each drive motor 430. Control system 412 may include a drive motor encoder 428 in communication with drive motor 430 and motor control system 412 for information regarding operation of the drive motor 430 to the motor control system 412.

Control system 412 may include auxiliary actuator and sensor devices 432. Auxiliary actuator and sensor devices 432 may include, for example, a compass, gyro, accelerometer, wireless router, wireless mouse, wireless keyboard, walker actuators, wheelchair actuators, thermoelectric coolers, and/or auxiliary display actuator and sensor devices for collecting or receiving information.

Referring to FIG. 20, control system 412 may include safety system 434 in communication with robot central processing unit 414. Safety system 434 may include, for example, a respective processor, memory, system bus and wired connections, and/or a communications transceiver. Safety system 434 may include one or more primary sensors such as, for example, bumper switch 446, LIDAR sensor 448, ultrasonic sensor 450, infrared sensor 452, 3D infrared camera 454, warning lights 456, driving lights 458, tilt sensors 436, cliff sensors 438, walker sensors 440, wheelchair sensors 442 and/or other auxiliary sensors 444 for collecting or receiving information.

Referring to FIG. 20, control system 412 may include one or more wireless communications interfaces and/or communications transceivers configured for communications via suitable communications protocols with compatible communications networks (not shown in FIG. 20). Communications transceivers may include, for example, Wi-fi transceiver 468, smart Bluetooth transceiver 466, Zigbee transceiver 464, wireless antenna transceiver 462, and/or GPS/RF transceiver 460.

The invention claimed is:

1. A convertible telepresence robot system comprising:
 a monitor, monitor bracket, right column top portion, right drive column, lower-rear safety bumper, left drive column, upper rear safety bumper, left column top portion, camera, support panel, a left and a right primary wheel, and at least one secondary wheel;
 the support panel being supported at a first end by the left drive column, and a second end, opposite the first end, by the right drive column;
 the lower-rear safety bumper connected to a lower rear portion of a bottom end of the left drive column to a lower rear portion of a bottom end of the right drive column;
 the upper-rear safety bumper connected to an upper rear portion of a top end of the left drive column and to an upper rear portion of a top end of the right drive column;
 a first primary wheel rotatably connected to a front portion of the bottom end of the left drive column and a second primary wheel rotatably connected to a front portion of the bottom end of the right drive column;
 a monitor bracket engaging a top portion of the support panel;
 a monitor supported by the monitor bracket;
 the left column top portion supported by a top surface of the left drive column, the right column top portion supported by a top surface of the right drive column; and
 a camera engageable with a top surface of at least one of the left column top portion and the right column top portion.

2. The system of claim 1 further comprising a left and right railing extension, a left and right upper lateral support, a left and right lower lateral support, a left and right tertiary wheel, and at least one hand brake;
 a first end of the left lower lateral support removably coupled to the left primary wheel, a bottom surface of the left lower lateral support rotatably connected to the left tertiary wheel, a first end of the right lower lateral support removably coupled to the right primary wheel, a bottom surface of the right lower lateral support rotatably connected to the right tertiary wheel;
 a first end of the left upper lateral support removably coupled to the left drive column at an upper receiver point, a first end of the right upper lateral support removably coupled to the right drive column at an upper receiver point;
 a top end of the left railing extension removably connected to the left column top portion, a bottom end of the left railing extension removably connected to a top surface of the left lower lateral support, the left railing extension traversing an aperture in the left upper lateral support at a point between the top end of the left railing extension and the bottom end of the left railing extension;
 a top end of the right railing extension removably connected to the right column top portion, a bottom end of the left railing extension removably connected to a top surface of the right lower lateral support, the right railing extension traversing an aperture in the right upper lateral support at a point between the top end of the right railing extension and the bottom end of the right railing extension;
 the at least one hand brake removably engaged with at least one of the left column top portion and the right column top portion at a point below the top end of the respective railing extension.

3. The system of claim 2 further comprising a seat portion, a left foot support, a right foot support, and a control system;

the seat portion connected to and supported between the left drive column and the right drive column at a point between the upper-rear safety bumper and the lower-rear safety bumper;

the left foot support connected to the left lower lateral support, and extending towards the right lower lateral support;

the right foot support connected to the right lower lateral support, and extending towards the left lower lateral support; and the control system integrated into at least one of the left upper lateral support and the right upper lateral support.

4. The system of claim 3 further comprising a left hand grip, a right hand grip, and a secondary monitor;

the left hand grip affixed to the left railing extension at a point above the left upper lateral support;

the right hand grip affixed to the right railing extension at a point above the right upper lateral support; and the secondary monitor pivotably connected to one of the left railing extension and the right railing extension at a point above the respective hand grip.

5. The system of claim 1 wherein the monitor bracket is configured to move up and down a portion of the left drive column and the right drive column, thereby allowing the monitor to be raised or lowered.

6. The system of claim 1 further comprising a storage basket may be connected to and supported between the left drive column and the right drive column at a position between the lower-rear safety bumper and the upper-rear safety bumper.

7. The system of claim 3 wherein the seat portion may pivot from a first position in which the seat portion is coplanar with a plane defined by the left drive column and the right drive column to a second position in which the seat portion is perpendicular to the plane defined by the left drive column and the right drive column.

8. The system of claim 3 wherein the left foot support and the right foot support may independently pivot from a first position in which the left and right foot supports are coplanar with a plane defined by the left lower lateral support and the right lower lateral support to a second position in which the left and right foot supports are perpendicular to the plane defined by the left lower lateral support and the right lower lateral support.

9. The system of claim 2 further comprising a cup-holder integrated into at least one of the left upper lateral support and the right upper lateral support.

10. The system of claim 9 wherein the cup-holder may use electricity to perform at least one of heating and cooling of an object placed therein.

11. The system of claim 2 further comprising at least one of: a heart rate sensor, a blood pressure sensor, and a thermal sensor, integrated into at least one of the left railing extension and the right railing extension.

12. The system of claim 1, wherein the first and second primary wheel may rotate in a horizontal axis to enable the system to move laterally (sideways).

13. The system of claim 3, wherein the control system comprises a joystick.

14. A convertible telepresence robot system comprising:

a configurable frame assembly;

a set of wheels supporting the configurable frame assembly for rolling movement across a floor, the set of wheels comprising a primary wheel powered for driving engagement with the floor;

a battery power supply supported for movement in common with the configurable frame assembly relative to the floor;

an electric motor operably connected to the battery power supply, the electric motor in driving relationship with the primary wheel for driving rolling movement of the convertible telepresence robot system relative to the floor; and a control system comprising a processor coupled to memory and operable for executing a drive system control algorithm to control movement of the primary wheel to selectably start and stop rolling movement of the convertible telepresence robot system relative to the floor, the control system comprising a collision avoidance sensor and a collision avoidance algorithm to stop driving motion of the primary wheel;

the configurable frame assembly selectively configurable between an independent assistive base configuration, a walker configuration including railing extensions, and a wheelchair configuration including a seat portion.

15. The system of claim 14, wherein, when in the walker configuration, the control system configured to receive walking position information.

16. The system of claim 14 additionally comprising a monitor, the monitor supported by the convertible frame assembly and facing a point between and above the railing extensions, while in the walker configuration.

17. The system of claim 14, wherein the battery power supply and the electric motor are housed within a drive column member of the convertible frame assembly.

18. The system of claim 17, wherein the drive column member is configured to support a respective upper end portion of the railing extensions.

19. The system of claim 18, wherein the drive column member is supported by the primary wheel at a bottom end portion of the drive column member.

* * * * *